US005993388A

United States Patent [19]

Kattan et al.

[11] Patent Number: 5,993,388

[45] Date of Patent: Nov. 30, 1999

[54] NOMOGRAMS TO AID IN THE TREATMENT OF PROSTATIC CANCER

[76] Inventors: Michael W. Kattan, 4831 McDermed, Houston, Tex. 77035; Peter T. Scardino, 1111 Hermann Dr.,14B, Houston, Tex. 77004

[21] Appl. No.: 09/104,218

[22] Filed: Jun. 25, 1998

Related U.S. Application Data

[60] Provisional application No. 60/051,428, Jul. 1, 1997.

[51] Int. Cl.$^{6}$ .......... A61B 5/00

[52] U.S. Cl. .......... 600/300; 128/898

[58] Field of Search .......... 600/300; 128/897, 128/898, 920, 923, 924

[56] References Cited

PUBLICATIONS

M. W. Kattan, et al., "Evaluation of a Nomogram Used to Predict the Pathologic Stage of Clinically Localized Prostate Carcinoma", *Cancer*, vol. 79(3), pp. 528–537 (1997).

R. A. Badalament, et al., "An Algorithm For Predicting Nonorgan Confined Prostate Cancer Using the Results Obtained From Sextant Core Biopsies with Prostate Specific Antigen Level", *The Journal of Urology*, vol. 156, pp. 1375–1380 (1996).

P. Narayan, et al., "The Role of Transrectal Ultrasound––Guided Biopsy–Based Staging, Preoperative Serum Prostate–Specific Antigen, and Biopsy Gleason Score in Prediction of Final Pathologic Diagnosis in Prostate Cancer", *Urology*, vol. 46(2), pp. 205–212 (1995).

D.G. Bostwick et al., "Optimized Microvessel Density Analysis Improves Prediction of Cancer Stage from Prostate Needle Biopsies", *Urology*, vol. 48(1), pp. 47–57 (1996).

A. W. Partin, et al., "Selection of Men at High Risk for Disease Recurrence For Experimental Adjuvant Therapy Following Radical Prostatectomy", *Urology*, vol. 45(5), pp. 831–838 (1995).

F.E. Harrell, Jr., et al., "Tutorial in Biostatistics; Multivariable Prognostic Models: Issues in Developing Models, Evaluating Assumptions and Adequacy, and Measuring and Reducing Errors", *Statistics in Medicine*, vol. 15, pp. 361–387, (1996).

A. W. Partin, et al., "The Use of Prostate Specific Antigen, Clinical Stage and Gleason Score to Predict Pathological Stage in Men with Localized Prostate Cancer", *The Journal of Urology*, vol. 150, pp. 110–114 (1993).

A. W. Partin , et al., "Combination of Prostate–Specific Antigen, Clinical Stage, and Gleason Score to Predict Pathological Stage of Localized Prostate Cancer", *JAMA*, vol. 227(18), pp.14451451 (1997).

J.J. Bauer, et al., "Biostatistical Modeling Using Traditional Variables and Genetic Biomarkers for Predicting the Risk of Prostate Carcinoma recurrence after Radical Prostatectomy", *Cancer*, vol. 79(5), pp. 952–962 (1997).

J.J. Bauer et al., "Biostatistical Modeling Using Traditional Preoperative and Pathological Prognostic Variables in the Selection of Men at High Risk for Disease Recurrence after Radical Prostatectomy for Prostate Cancer", *The Journal of Urology*, vol. 159, pp. 929–933 (1998).

*Primary Examiner*—Eric F. Winakur

*Attorney, Agent, or Firm*—Baker & Botts LLP; James Remenick

[57] ABSTRACT

This invention relates to methods and apparatus for predicting probability of cancer recurrence following radical prostatectomy using predetermined clinical and pathological factors. The invention includes nomograms which can be used preoperatively and postoperatively in patients diagnosed with prostatic adenocarcinoma to aid in selection of an appropriate course of therapy.

32 Claims, 7 Drawing Sheets

© 1997 Michael W. Kattan and Peter T. Scardino
Baylor College of Medicine

NOMOGRAMS TO AID IN THE TREATMENT OF PROSTATIC CANCER

REFERENCE TO RELATED APPLICATIONS

This patent application is a continuation of U.S. provisional patent application, Ser. No. 60/051,428, filed Jul. 1, 1997.

RIGHTS IN THE INVENTION

This invention was supported, in part, by grant number CA 58204 awarded by the National Cancer Institute, and the United States Government may have certain rights in the invention.

AUTHORIZATION REGARDING COPYRIGHT

A portion of the disclosure of this patent document contains material which is subject to copyright protection. The copyright owner has no objection to the facsimile reproduction by anyone of the patent document or the patent disclosure, as it appears in the United States Patent and Trademark Office patent file or records, but otherwise reserves all copyright rights whatsoever.

BACKGROUND OF THE INVENTION

1. Field of the Invention

This invention relates to methods and apparatuses for predicting probability of disease recurrence following radical prostatectomy using predetermined clinical and pathological factors. The invention includes nomograms that can be used preoperatively and postoperatively to aid in selection of an appropriate course of therapy.

2. Description of Background

Prostate adenocarcinoma is the most common malignancy in males over the age of 50. Clinically localized prostate cancer is most often treated with conservative management (G. W. Chodak et al., N Engl J Med 330:242–248, 1994; P. C. Albertson et al., JAMA 274:626–63, 1995), external beam irradiation (G. E. Hanks et al., J Urol 154:456–9, 1995; M. A. Bagshaw et al., J Urol 152:1781–5, 1994), or radical prostatectomy (M. Ohori et al., J Urol 154:1818–24, 1995; G. S. Gerber et al., JAMA 276:615–9, 1996; C. R. Pound et al., Urol Clin North Am 24:395–406, 1997; J. G. Trapasso et al., J Urol 152:1821–5, 1996), and occasionally with therapeutic interventions such as interstitial radioactive seed implantation or cryotherapy. Making a decision among the different management choices for clinically localized prostate cancer would be greatly facilitated if reliable predictors of the probability that the selected treatment would control the cancer long term were available. Currently, there are no satisfactory randomized prospective trials comparing cancer control among alternative treatments. Although clinical trials are underway, even when these trials are completed, all patients with a clinically localized cancer will not have an equal probability of a successful outcome.

a. Preoperative Assessment

Prior to undergoing radical prostatectomy, it is of great interest to the patient to know whether the procedure is likely to be curative. Because the pathologic stage of cancer correlates with the probability of recurrence after surgery, a number of investigators have made efforts based on cohort studies to predict the final pathologic stage of prostate cancer using various parameters. A number of nomograms and algorithms have been formulated in an effort to identify the pathological stage of an individual's prostatic cancer. For instance, Partin, et al., has developed a nomogram based on pretreatment prostate specific antigen level (PSA), tumor grade, and clinical stage, to aid physicians in making treatment recommendations by predicting the probability of the final pathological stage of clinically localized prostate carcinoma. (A. W. Partin et al., J Urol 115:110–4, 1993). This nomogram was based on data for one patient population. However, although this nomogram does discriminate between organ-confined and non-confined cancer, it has difficulty predicting high probabilities of seminal vesicle invasion and lymph node metastasis, which are the pathologic features with the most profound impact on prognosis. (M. Kattan et al., Cancer 79:528–537, 1997). In addition, this type of nomogram, including the updated version (Partin et al., JAMA 277:1445–1451, 1997), does not provide the physician with a simple means of advising a patient of the likelihood of recurrence if a radical prostatectomy is performed.

Another algorithm developed pursuant to a study by Badalament et al., purports to predict non-organ confined prostate cancer. This study found that nuclear grade, preoperative PSA, total percent tumor involvement, number of positive sextant cores, preoperative Gleason score, and involvement of more than five percent of a base and/or apex biopsy were significant for prediction of disease organ confinement status. (R. Badalament et al., J Urol 156:1375–1380, 1996).

Another predictor by Narayan et al., uses preoperative serum PSA, biopsy Gleason score, and biopsy-based stage to predict final pathological stage, by constructing probability plots. (P. Narayan et al., Urology 46:205–212, 1995). Yet another predictor by Bostwick et al., uses PSA concentrations, optimized microvessel density of needle biopsy samples and Gleason score to predict extra-prostatic extension. (David Bostwick et al., Urology 48:47–57, 1996).

Existing preoperative predictors typically use final pathologic stage as their end point. (A. W. Partin et al., JAMA 277:1445–1451, 1997). This point is problematic in that some patients with apparently organ confined disease will later develop disease recurrence, whereas many patients with non-organ confined disease will remain disease free. (M. W. Kattan et al., Cancer 793:528–537, 1997). Extracapsular tumor extension, positive surgical margins, seminal vesicle involvement and positive pelvic lymph nodes are adverse pathological features. (A. W. Partin et al., Urol Clin North Am 204:713–725, 1993; J. I. Epstein et al., Cancer 71:3582–3593, 1993; A. Stein et al., J Urol 147:942, 1992). Yet not all patients with one or more of these findings are destined to have disease recurrence after radical prostatectomy. Of the 462 men evaluated by Partin et al. with either focal or established extracapsular penetration (A. W. Partin et al., Urol Clin North Am 20(4):713–725, 1993), only 80 (17%) had evidence of disease recurrence with a mean follow-up of 53 months (range 12 to 120 months). Similarly, Ohori and colleagues report a five-year PSA progression rate of 25% for patients with extracapsular extension in the radical prostatectomy specimen. (M. Ohori et al., Cancer 74:104–14, 1994). In a study of the association between positive surgical margins and disease progression, Epstein et al. found that only half of their patients with positive margins developed disease recurrence. (J. I. Epstein et al., Cancer 71:3582–3593, 1993). Thus, using final pathologic stage as an end point limits the utility of a nomogram to accurately predict disease recurrence following radical prostatectomy. In addition, although final pathology has been associated with eventual treatment failure, none of the existing predictors allow the physician to accurately predict preoperatively the likelihood of recurrence of cancer in a patient if a radical prostatectomy is performed. This is typically the information of greatest interest to the patient before electing to undergo surgery.

There are several established prognostic factors relating to the risk of recurrence after surgery or radiotherapy or the risk of metastasis or death from cancer after conservative management, including clinical stage (M. Ohori et al., Cancer 74:104–14, 1994), Gleason grade (P. C. Albertson et al., JAMA 274:626–631, 1995; G. E. Hanks et al., J Urol 154:456–9, 1995; G. S. Gerber et al., JAMA 276:615–9, 1996) and serum prostate specific antigen (PSA) levels. (G. K. Zagars, Cancer 73:1904–12; 1994). Prior to the present invention, these three routinely available prognostic factors had not been successfully combined into a risk profile that could be used to predict, prior to surgery, the probability of recurrence or metastatic progression after surgical management.

b. Post-Operative Assessment

The most common aggressive therapy for the treatment of clinically localized prostate cancer is radical prostatectomy. Unfortunately, approximately one third of men treated with radical prostatectomy later experience progression of their disease. Typically, the first indication that the disease has progressed occurs as a detectable level of serum PSA months or years following surgery. Early identification, prior to detectable PSA, of men likely to ultimately experience progression would be useful in considering adjuvant therapy or, before documented progression, when adjuvant therapy may be most effective. Accurate identification of the probability of recurrence would also be particularly useful in clinical trials to assure comparability of treatment and control groups or to identify appropriate candidates for investigational treatment such as gene therapy.

Traditionally, the judgment of which patients are at high risk for failure following radical prostatectomy has been based largely on final pathologic stage. As noted, final pathologic stage alone (A. W. Partin et al., JAMA 277:1445–1451, 1997) is a problematic variable for judging high-risk disease since some patients with apparently organ-confined cancer will later develop disease recurrence, and many patients with non-organ-confined cancer will remain disease-free (C. R. Pound et al., Urol Clin North Am 24:395–406, 1997). Not all patients with extracapsular extension or seminal vesicle involvement are destined to have disease recurrence after radical prostatectomy (M. Ohori et al., Cancer 74:104–14, 1994; M. Ohori et al., J Urol 154:1818–1824, 1995; C. R. Pound et al., Urol Clin North Am 24:395–406, 1997; J. G. Trapasso et al., J Urol 152:1821–1825, 1994; A. W. Partin et al., Urol Clin North Am 20:713–725, 1993; J. I. Epstein et al., Cancer 71:3582–3593, 1993). Thus, the use of individual pathologic features appears insufficient to estimate probability for recurrence; a method of combining them is needed.

In 1995, Partin and colleagues (A. W. Partin et al., Urology 45:831–838, 1995) published a model for predicting relative risk that was derived using 216 men with clinical stage T2b and T2c prostate cancer treated by a single urologist. The model utilized pretreatment serum PSA with a sigmoidal transformation, radical prostatectomy Gleason score (Gleason sum), and pathologic stage as specimen confined or nonspecimen confined to identify patients with a high relative risk of recurrence following surgery. Their model computed log relative risk and categorized patients into low, intermediate, and high. In a validation cohort of 214 patients treated by one of three different urologists at two institutions, Partin was able to illustrate that the model was apparently able to stratify those patients as well, based on their Kaplan-Meier PSA recurrence-free survival rates although no statistical testing of strata differences was performed. Bauer et al. (J. J. Bauer et al., J Urol 159:929–933, 1998) recently emulated Partin's approach with 378 patients but added race as a predictor variable and widened the cohort to include all clinical stages up to T1a through T2c. Another difference with the Bauer model was the cutoffs used to distinguish the risk groups (relative risks of 4.0 and 5.75 for Partin versus 10 and 30 for Bauer). Bauer's validation cohort of 99 men indicated a difference in survival rates between the low- and high-risk groups but no difference between intermediate risk and either low or high risk. In another recent study, Bauer (J. J. Bauer et al., Cancer 79(5):952–962, 1997) added biomarkers p53, Ki-67, and bcl-2 to the relative risk calculation. Finally, Harrell et al., discloses a nomogram which evaluates estrogen as a treatment for prostate cancer. This nomogram uses numerous variables, such as age, weight index, blood pressure data, history of cardiovascular disease, tumor size, tumor grade and serum prostatic acid phosphatase to predict survival. (F. Harrell et al., Statistics in Medicine 15:361–387, 1996).

However, none of the postoperative models currently available predict probability of recurrence. Moreover, prior to the present invention, there has been no method or means to predict the probability of treatment failure following surgery, defined as a rising PSA level, following radical prostatectomy for clinically localized prostate cancer. Such risk profiles would be very useful in providing meaningful information to a patient making a decision among courses of therapy. Such a tool would provide the patient with his probability of recurrence instead of a relative risk which is more easily comprehended. While the relative risk informs the patient of his risk of recurring relative to another patient with certain characteristics, the actual probability should more greatly facilitate decision making for the patient.

Therefore, a need has arisen for a method and apparatus to accurately predict prior to surgery the likelihood of recurrence in an individual diagnosed with prostate cancer following radical prostatectomy, using routinely available clinical variables. In addition, a need has arisen for a method and apparatus for accurately predicting probability of recurrence post-prostatectomy, using data routinely collected and available immediately postoperatively, to evaluate whether adjuvant therapy may be warranted before PSA begins to rise.

SUMMARY OF THE INVENTION

The present invention is directed to methods and apparatuses for predicting probability of disease recurrence following radical prostatectomy using routinely performed and available factors. The invention includes nomograms that can be used preoperatively and postoperatively to aid in selection of an appropriate course or courses of therapy.

One embodiment of the invention is directed to a method for predicting probability of recurrence of prostatic cancer following radical prostatectomy in a patient diagnosed as having prostatic cancer. This method comprises the steps of correlating a selected set of preoperative factors determined for each of a plurality of persons previously diagnosed with prostatic cancer and having been treated by radical prostatectomy with the incidence of recurrence of prostatic cancer for each person of said plurality of persons to generate a functional representation of the correlation, wherein said selected set of preoperative factors comprises pretreatment PSA level, combined Gleason grade in the biopsy specimen and clinical stage, and matching an identical set of preoperative factors determined from the patient diagnosed as having prostatic cancer to the functional representation to predict the probability of recurrence of prostatic cancer in the patient following radical prostatectomy. In another embodiment, biopsy Gleason sum may be used instead of combined Gleason grade. In another embodiment, the factors may further comprise one or more of the following: total length of cancer in the biopsy cores; maximum cancer length in a core; and apoptotic index.

Another embodiment of the invention is directed to a postoperative method for predicting probability of recurrence of prostatic cancer in a patient who has previously undergone a radical prostatectomy. This method comprises the steps of correlating a selected set of factors determined for each of a plurality of persons previously diagnosed with prostatic cancer with the incidence of recurrence of prostatic cancer for each person of said plurality to generate a functional representation of the correlation, wherein said selected set of factors comprises preoperative PSA level, specimen Gleason sum, prostatic capsular invasion level, surgical margin status, presence of seminal vesicle invasion, and lymph node status, wherein said plurality of persons comprises men having undergone radical prostatectomy, and matching an identical set of factors determined from the patient to the functional representation to predict the probability of recurrence of prostatic cancer for the patient.

Additional embodiments of the invention are directed to nomograms for determining a preoperative probability of prostatic cancer recurrence such as those depicted in FIGS. 2A and 2B and methods of using these nomograms to predict a patient's prognosis. One such method predicts a patient's preoperative prognosis by matching a patient-specific set of preoperative factors comprising pretreatment PSA level, clinical stage, and combined Gleason grade to the nomogram depicted in FIG. 2A or FIG. 2B and determining the preoperative prognosis of the patient.

Additional embodiments of the invention are directed to a nomogram for determining a postoperative probability of prostatic cancer recurrence such as depicted in FIG. 5 and methods of using this nomogram to predict a patient's prognosis. One such method predicts a patient's postoperative prognosis following radical prostatectomy by matching a patient-specific set of factors comprising the patient's preoperative PSA level, specimen Gleason sum, prostatic capsular invasion level, surgical margin status, presence of seminal vesicle invasion, and lymph node status to the nomogram depicted in FIG. 5 and determining the prognosis of the patient.

Another embodiment of the invention is directed to a method for determining a need for an adjuvant therapy in a patient following radical prostatectomy comprising the steps of: determining a set of factors on the patient, the set of factors comprising the patient's preoperative PSA level, specimen Gleason sum, prostatic capsular invasion level, surgical margin status, presence of seminal vesicle invasion, and lymph node status; and matching the set of factors to the nomogram depicted in FIG. 5 to determine whether the adjuvant therapy is needed in view of the probability of recurrence.

Another embodiment of the invention is directed to an apparatus for predicting probability of disease recurrence in a patient with prostatic cancer following a radical prostatectomy, wherein the apparatus comprises: a correlation of preoperative factors determined for each of a plurality of persons previously diagnosed with prostatic cancer and having been treated by radical prostatectomy with incidence of recurrence of prostatic cancer for each person of said plurality of persons, wherein said selected set of preoperative factors comprises pretreatment PSA level, combined Gleason grade in the biopsy specimen and clinical stage; and a means for matching an identical set of preoperative factors determined from the patient diagnosed as having prostatic cancer to the correlation to predict the probability of recurrence of prostatic cancer in the patient following radical prostatectomy.

Another embodiment of the invention is directed to an apparatus for predicting probability of disease recurrence in a patient with prostatic cancer following a radical prostatectomy, wherein the apparatus comprises: a correlation of clinical and pathological factors determined for each of a plurality of persons previously diagnosed with prostatic cancer and having been treated by radical prostatectomy with incidence of recurrence of prostatic cancer for each person of said plurality of persons wherein said selected set of factors comprises preoperative PSA level, specimen Gleason sum, prostatic capsular invasion level, surgical margin status, presence of seminal vesicle invasion, and lymph node status; and a means for matching an identical set of factors determined from the patient diagnosed as having prostatic cancer to the correlation to predict the probability of recurrence of prostatic cancer in the patient following radical prostatectomy.

Still another embodiment of the invention is directed to a nomogram for the graphic representation of the probability that a patient with prostate cancer will remain free of disease following radical prostatectomy comprising a substrate or a solid support and a set of indicia on the substrate or solid support, the indicia comprising a pretreatment PSA level line, a clinical stage line, a combined Gleason grade line, a points line, a total points line and a predictor line, wherein said pretreatment PSA level line, clinical stage line and combined Gleason grade line each have values on a scale which can be correlated with values on a scale on the points line, and wherein said total points line has values on a scale which may be correlated with values on a scale on the predictor line, such that the value of each of the points correlating with the patient's pretreatment PSA level, combined Gleason grade, and clinical stage can be added together to yield a total points value, and the total points value can be correlated with the predictor line to predict the probability of recurrence.

Still another embodiment of the invention is directed to a nomogram for the graphic representation of the probability that a patient with prostate cancer will remain free of disease following radical prostatectomy comprising a substrate or solid support and a set of indicia on the substrate or solid support, the indicia comprising a preoperative PSA level line, a specimen Gleason sum line, a prostatic capsular invasion level line, a surgical margin status line, a presence of seminal vesicle invasion line, a lymph node status line, a points line, a total points line and a predictor line, wherein said preoperative PSA level line, specimen Gleason sum line, prostatic capsular invasion level line, surgical margin status line, presence of seminal vesicle invasion line, and lymph node status line each have values on a scale which can be correlated with values on a scale on the points line, and wherein said total points line has values on a scale which may be correlated with values on a scale on the predictor line, such that the value of each of the points correlating with the patient's preoperative PSA level, specimen Gleason sum, prostatic capsular invasion level, surgical margin status, presence of seminal vesicle invasion, and lymph node status can be added together to yield a total points value, and the total points value can be correlated with the predictor line to predict the probability of recurrence.

Other embodiments and advantages of the invention are set forth, in part, in the description which follows and, in part, will be obvious from this description and may be learned from the practice of the invention.

DESCRIPTION OF THE INVENTION

Figure 1:
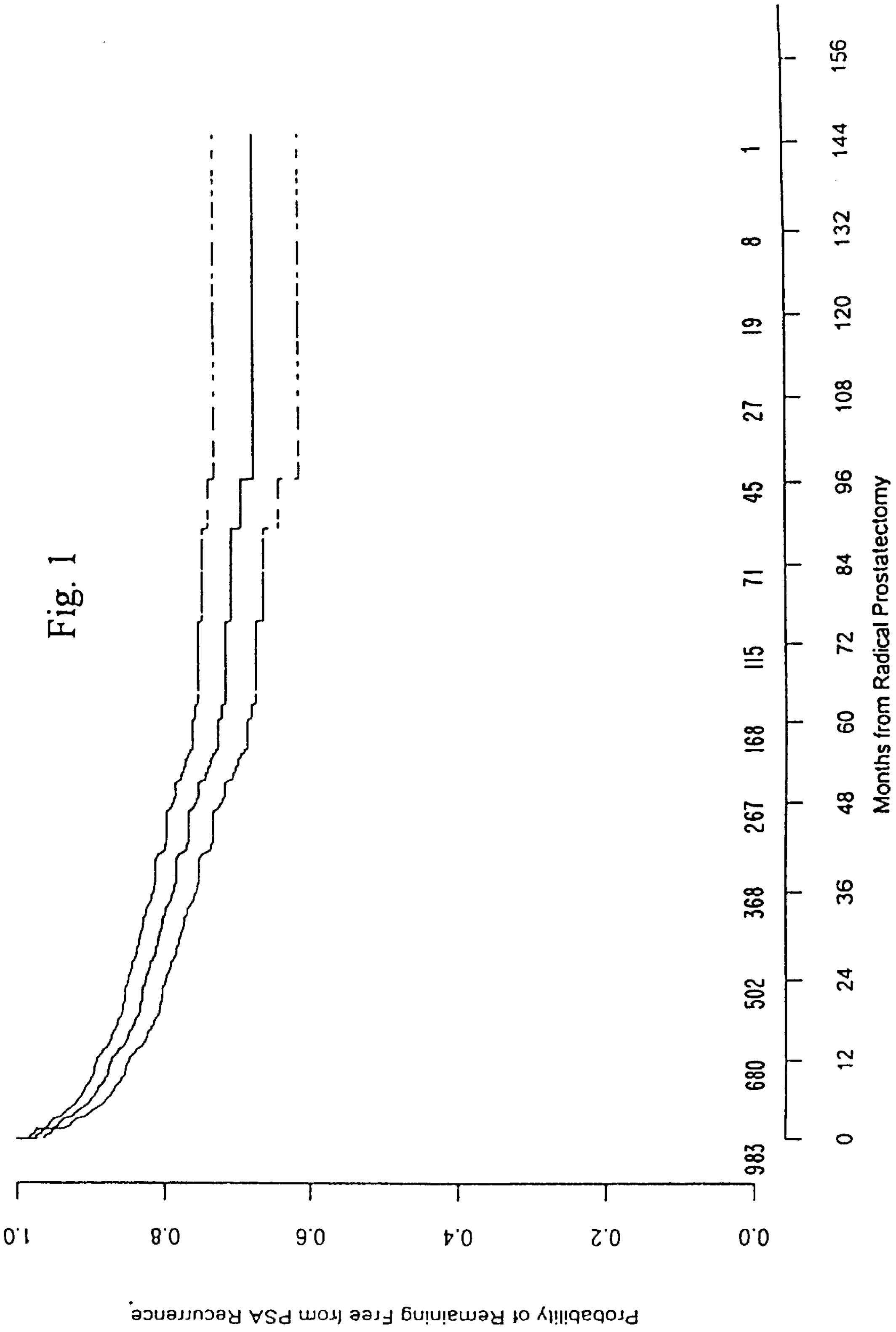
FIG. 1 Graph of overall recurrence-free probabilities following radical prostatectomy for the preoperative nomograms of FIGS. 2A and 2B.

As embodied and broadly described herein, the present invention is directed to methods and apparatus for predicting probability of disease recurrence following radical prostatectomy using routinely performed factors. The invention includes nomograms that can be used preoperatively and postoperatively to aid in selection of an appropriate course or courses of therapy.

a. Embodiments Using Preoperative Variables

The present invention provides for nomograms to predict disease recurrence using clinical factors available prior to surgery, to aid patients considering radical prostatectomy to treat clinically localized prostate cancer. The preoperative nomograms predict probability of disease recurrence after radical prostatectomy for localized prostate cancer (cT1-T3a N0 or NX M0 or MX) using routinely available preoperative factors, to assist the physician and patient in deciding whether or not radical prostatectomy is an acceptable treatment option. The present invention also provides for postoperative nomograms using selected variables. These nomograms can be used in clinical decision making by the clinician and patient and can be used to identify patients at high risk of disease recurrence who may benefit from neoadjuvant treatment protocols.

With respect to the preferred embodiments of the preoperative nomogram, using Cox proportional hazards regression, clinical data and disease follow-up were modeled for 983 men with clinical stage cT1-T3a N0 or NX M0 or MX prostate cancer who were treated with radical prostatectomy at The Methodist Hospital in Houston, Tex. Clinical data included pretreatment prostate specific antigen, biopsy Gleason scores, and clinical stage. Treatment failure was recorded when there was either clinical evidence of disease recurrence, a rising serum prostate specific antigen level of 0.4 ng/mL or greater, or initiation of adjuvant therapy. Validation was performed on this set of men as well as a separate sample of 168 men, also from The Methodist Hospital. Both groups of men came from the SPORE Prostate Information System database.

The 983 men modeled were selected from a group of 1055 patients. Specifically, 1055 patients admitted between June 1983 and December 1996 to The Methodist Hospital with the intent to treat their clinically localized prostate cancer (cT1-T3a N0 or NX M0 or MX) with radical retropubic prostatectomy (RRP) were potential candidates for this analysis. One urologist treated all patients. Pelvic lymph node dissections were performed on all men, and RRP was aborted in 24 of 55 patients who were found to have positive nodes prior to RRP. These men were not excluded from analysis. Excluded from analysis were 55 men initially treated with definitive radiotherapy, and 1 treated with cryotherapy, who had a "salvage" radical prostatectomy for delayed local recurrence of cancer. (E. Rogers et al., J Urol 153:104–10, 1995). Sixteen men had no disease follow-up information and were also excluded. For comparison with other series, and not used as predictor or outcome variables, the final pathologic stage (M. Ohori et al., Cancer 74:104–14, 1994) distribution of the remaining 983 men was the following: pT1-2N0 (54.2%), pT3a,bN0 (27.1%), pT3cN0 (9.1%), and pT1-3N+ (9.6%). Surgical margins were reported as positive in 15%. The mean age was 63 years (range 38–81), and 85% of the patients were Caucasian. The following routinely performed clinical variables were selected as predictors of recurrence: pretreatment serum PSA levels, primary and secondary Gleason grade in the biopsy specimen (D. F. Gleason, Urologic Pathology: The Prostate, 171–197, Tannebaum M., editor. Lea and Febiger 1997) and clinical stage (assigned using the TNM system) (M. Ohori et al., Cancer 74:104–14, 1994). The pretreatment PSA was the level measured by the Hybritech or comparable assay before biopsy when available. Otherwise, the PSA level measured in the study laboratory the fewest number of days before radical prostatectomy was used. Some patients treated before PSA came into routine clinical practice in 1987 had a serum bank specimen available for retrospective analysis in this laboratory. Biopsy Gleason grade and clinical stage were assigned by a single pathologist and urologist respectively. In the interest of a parsimonious model, emerging markers with less demonstrated predictive value (e.g., free PSA) were not included in this analysis. Missing values for PSA (N=75), and biopsy Gleason grade (N=16) were imputed using the transcan function in S-Plus software. (F. E. Harrell, Transcan: an S-Plus function, 1995; F. E. Harrell et al., Stats. Med 15:361–387, 1996). This approach uses all of the predictor variables to calculate the value of the missing variable without reference to the outcome. Imputing a missing value was preferred to deleting a patient's entire medical record, so that the maximum information is utilized and the bias that may result from a deleted case was avoided. (F. E. Harrell, Transcan: an S-Plus function, 1995; F. E. Harrell et al., Stats. Med 15:361–387, 1996). However, for comparison, a data set consisting of only complete records was modeled as well. The descriptive statistics after imputing appear in Tables 1–3.

Tables 1–3. Clinical characteristics of 983 patients undergoing radical retropubic prostatectomy after missing values were imputed. "UICC stage" refers to the preoperative clinical stages promulgated by Union International Contre le Cancer. (F. H. Schröder et al., The Prostate Supplement 4:129–138, 1992; M. Ohori et al., Cancer 74:104–14, 1994).

"N" refers to the number of patients in each category. "%" refers to the percent of all patients falling within the noted category.

TABLE 1

| UICC STAGE* | N (%) |
|---|---|
| T1a | 33 (3.3) |
| T1b | 50 (5.1) |
| T1c | 148 (15.1) |
| T2a | 266 (27.1) |
| T2b | 246 (25.0) |
| T2c | 182 (18.5) |
| T3a | 58 (5.9) |
| TOTAL | 983 (100) |

TABLE 2

| Gleason Grade in Biopsy** | | |
|---|---|---|
| Primary | Secondary | N (%) |
| 1–2 | 1–2 | 108 (11.0) |
| 1–2 | 3 | 158 (16.1) |
| 3 | 1–2 | 65 (6.6) |
| 3 | 3 | 340 (34.6) |
| 1–3 | 4–5 | 213 (21.7) |
| 4–5 | 1–5 | 99 (10.1) |

TABLE 3

| Pretreatment PSA*** | N (%) |
|---|---|
| 0.1–4.0 | 217 (22.1) |
| 4.1–10.0 | 472 (48.0) |
| 10.1–20.0 | 187 (19.0) |
| 20.1–100.0 | 107 (10.9) |

Median 6.8, Mean 9.9 ng/mL

*UICC Stage T1: clinically inapparent tumor, not palpable nor visible by imaging; T1a: tumor an incidental histologic finding, 5% or more of tissue resected; T1b: tumor an incidental histologic finding, less than 5% of tissue resected; T1c: tumor identified by needle biopsy (e.g., because of elevated serum prostate-specific antigen). UICC Stage T2: tumor confined within the prostate; T2a: tumor involves half a lobe or less; T2b: tumor involves more than half a lobe but not both lobes; T2c: tumor involves both lobes; T3: tumor extends through the prostate capsule; T3a: unilateral extracapsular extension.

**Gleason grades 1–2 are well differentiated, 3 is moderately differentiated, 4–5 are poorly differentiated.

***Median serum prostate — specific antigen (PSA) level for all patients 6.8 ng/mL (range, 0.1–100.0 ng/mL); mean serum PSA level for all patients, 9.9 ng/mL (95% confidence interval = 9.24 – 10.54 ng/mL).

Treatment failure was defined as either clinical evidence of cancer recurrence (observed in only 2 PSA-era patients before the PSA became detectable) or a postoperative PSA ≧0.4 ng/mL followed by a second PSA higher than the first. Patients who were treated with hormonal therapy (N=8) or radiotherapy (N=25) after surgery but before documented recurrence were treated as failures at the time of second therapy. Patients who had their RRP aborted due to positive nodes (N=24) were considered immediate treatment failures.

Figure 2A:
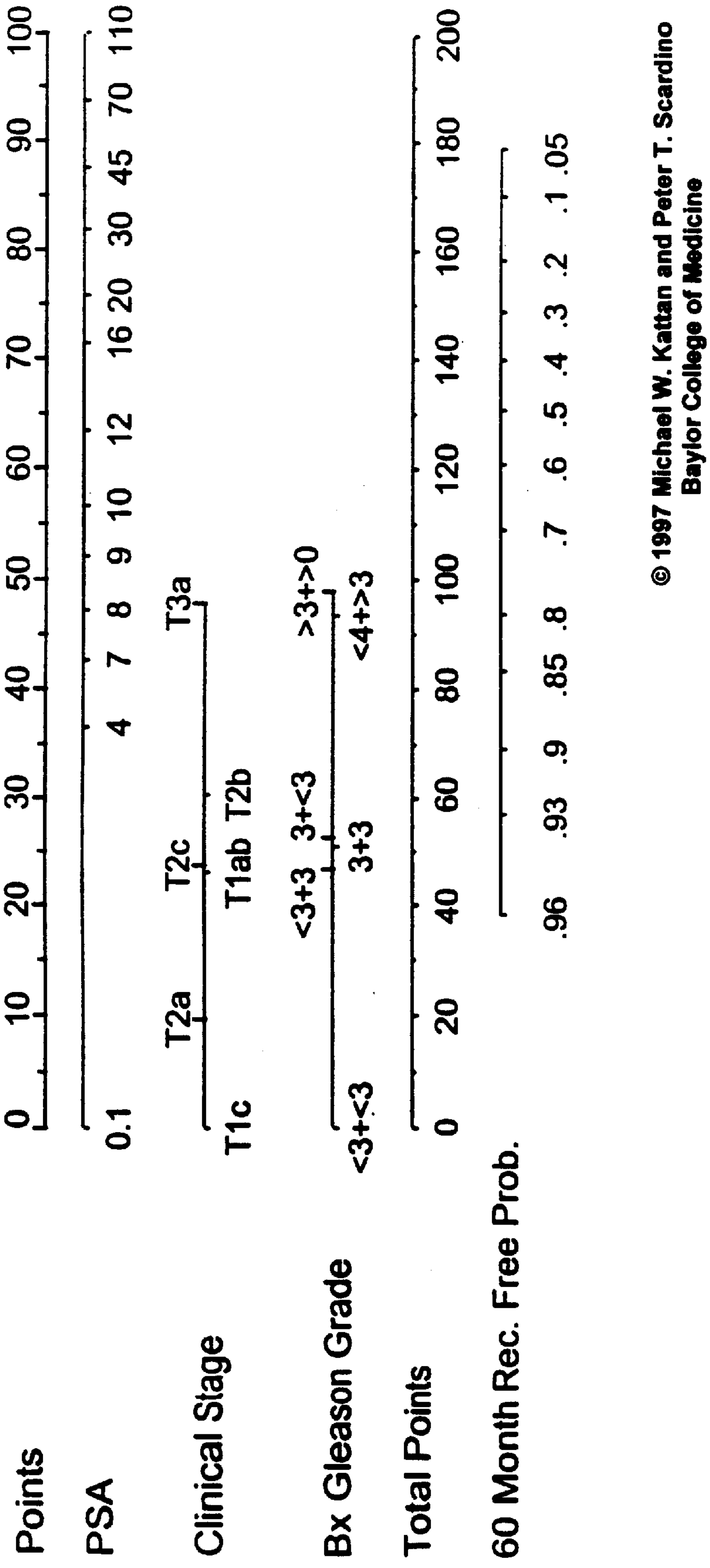
FIG. 2A A first nomogram useful for the preoperative assessment of probability of cancer recurrence following radical prostatectomy.
Figure 2B:
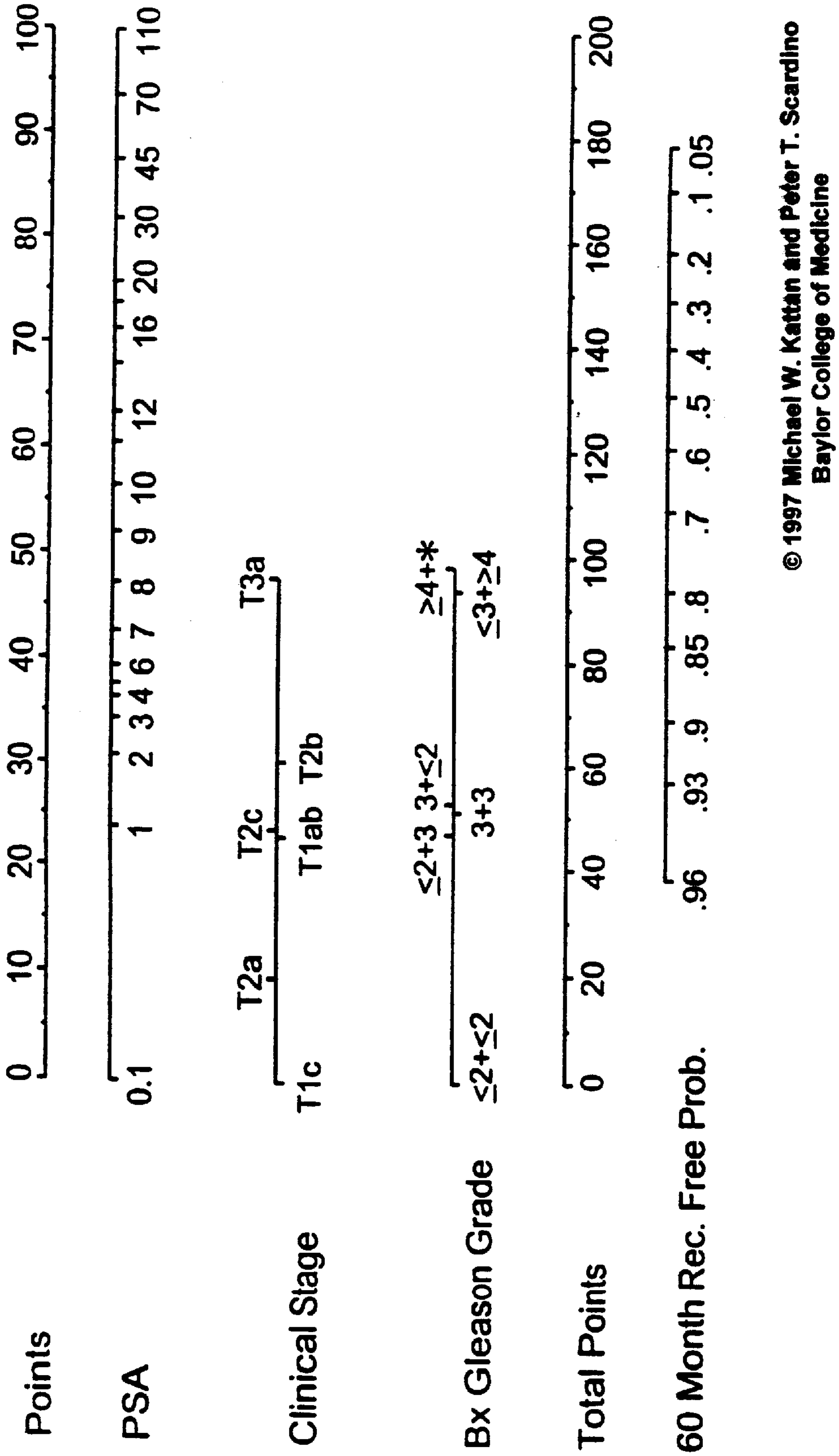
FIG. 2B A second nomogram useful for the preoperative assessment of probability of cancer recurrence following radical prostatectomy.

Estimates of the probability of remaining free from recurrence were calculated using the Kaplan-Meier method. Multivariable analysis was conducted using Cox proportional hazards regression. PSA had a skewed distribution and suspected nonlinear effect, so it was modeled as a restricted cubic spline (F. E. Harrell et al., Stats Med 15:361–387, 1996) of its log. Primary and secondary biopsy Gleason grades, each from 1 to 5, were collapsed into low (1–2), moderate (3), and high (4–5) grade categories due to small frequencies at the extremes. A potential interactive effect was anticipated due to the nature of the Gleason scoring system, so the Gleason primary and secondary grades were combined into 6 categories to come up with six combined Gleason grades in the biopsy specimen ("Bx Gleason Grade") In one embodiment of the nomogram the six categories used were: <3+<3, <3+3, 3+<3, 3+3, <4+>3 and >3+>0, based on frequency counts. (FIG. 2A). In another embodiment of the nomogram, the six categories were: ≦2+≦2, ≦2+3, 3+≦2, 3+3, ≦3+≧4, and ≧4+any, also based on frequency counts. (FIG. 2B). Similarly, clinical stages T1a (n=33) and T1b (n=50) were combined because of the small numbers of each and the similar method of detection of cancer. Decisions with respect to the coding of the nomogram variables were made prior to modeling. The Cox model was the basis for a nomogram.

Validation of the nomograms of FIGS. 2A and 2B contained three components. First, the nomograms were subjected to bootstrapping, with 200 re-samples, as a means of calculating a relatively unbiased measure of its ability to discriminate among patients, as quantified by the area under the receiver operating characteristic (ROC) curve. (J. A. Hanley et al., Radiology 143:29–36, 1982). With censored data, the ROC calculation (F. E. Harrell et al., Stats Med 15:361–387, 1996) is slightly modified from its normal method. Nonetheless, its interpretation is similar. The area under the ROC curve is the probability that, given two randomly drawn patients, the patient who recurs first had a higher probability of recurrence. Note that this calculation assumes that the patient with the shorter follow-up recurred. If both patients recur at the same time, or the non-recurrent patient has shorter follow-up, the probability does not apply to that pair of patients. The second validation component was to compare predicted probability of recurrence vs. actual recurrence (i.e., nomogram calibration) on the 983 patients, again using 200 bootstrap re-samples to reduce overfit bias which would overstate the accuracy of the nomogram. Finally, the third validation component was simply to apply the nomograms to the 168 patients not included in the modeling sample. These 168 patients were treated by 5 surgeons at Baylor College of Medicine. These were the patients with complete records only, and no values were imputed. As with the modeling sample, pretreatment PSA was measured with the Hybritech assay immediately before biopsy (if available) or before radical prostatectomy, and Gleason grading was done by a single pathologist. Each individual surgeon assigned the clinical staging in his/her patients. Patients were accrued between October 1990 and December 1996. For these patients, their predicted probability of 5 year recurrence was compared with actual follow-up, and the area under the ROC curve for these men was calculated. Statistical analyses were performed using S-Plus software (PC Version 3.3, Redmond Wash.) with the Design functions (F. E. Harrell, Programs available from statlib@lib.stat.cmu.edu, 1994).

Of the 983 patients analyzed, 196 had evidence of recurrence of prostate cancer following radical prostatectomy. For patients without disease recurrence, median and maximum follow-up were 30 and 146 months, respectively, and 168 patients had at least 60 months disease-free follow-up. Overall Kaplan-Meier recurrence-free probabilities and their 95% confidence intervals appear in FIG. 1. The x-axis depicts months from radical prostatectomy and the y-axis depicts probability of remaining free from PSA recurrence. Numbers above the months indicate patients at risk of recurrence. The cohort 5-year recurrence-free probability was 73% (95% CI: 69% to 76%). Consistent with previous analysis of the hazard rates (O. Dillioglugil et al., Urology 50:93–99, 1997), recurrence beyond the 5-year point is rare (average annual hazard rate=0.014/year). No recurrences were observed later than 100 months, but the tail of the curve is retained in FIG. 1 to illustrate follow-up. PSA, biopsy combined Gleason grade, and clinical stage were all associated with recurrence ($p<0.001$) for each, suggesting that the model with all three variables is likely superior to a smaller model (e.g., with PSA alone). Strong evidence for violation of the proportional hazards assumption was not seen in analyses and plots of the Schoenfeld residuals.

Two preoperative nomograms were constructed based on the Cox model and appear in FIGS. 2A and 2B. The nomograms are each used by first locating a patient's position on each predictor variable scale (PSA through clinical stage). Each scale position has corresponding prognostic points (top axis). For example, a PSA of 4 contributes approximately 37 points; this is determined by comparing the location of the 4 value on the PSA axis to the Points scale above and drawing a vertical line between the 2 axes. The point values for all clinical predictor variables can be determined in a similar manner and can be summed to arrive at a Total Points value. This value is plotted on the Total Points axis (second from the bottom). A vertical line drawn from the Total Points axis straight down to the 60-month recurrence free probability axis will indicate the patient's probability of remaining free from cancer recurrence for 5 years assuming he remains alive and does not die of another cause first.

The area under the ROC curve was computed for the nomograms. Without bootstrapping, the area was 0.76. Because this is the value on the same data used in modeling, it likely overstates expected performance on future data. After bootstrapping, the area was estimated to be 0.74. The probability of 5-year recurrence was predicted for the separate sample of 168 patients. Of these men, 12 had disease recurrence. Nomogram predictions were compared with actual outcome, and the area under the ROC curve was calculated and found to be 0.79.

Figure 3:
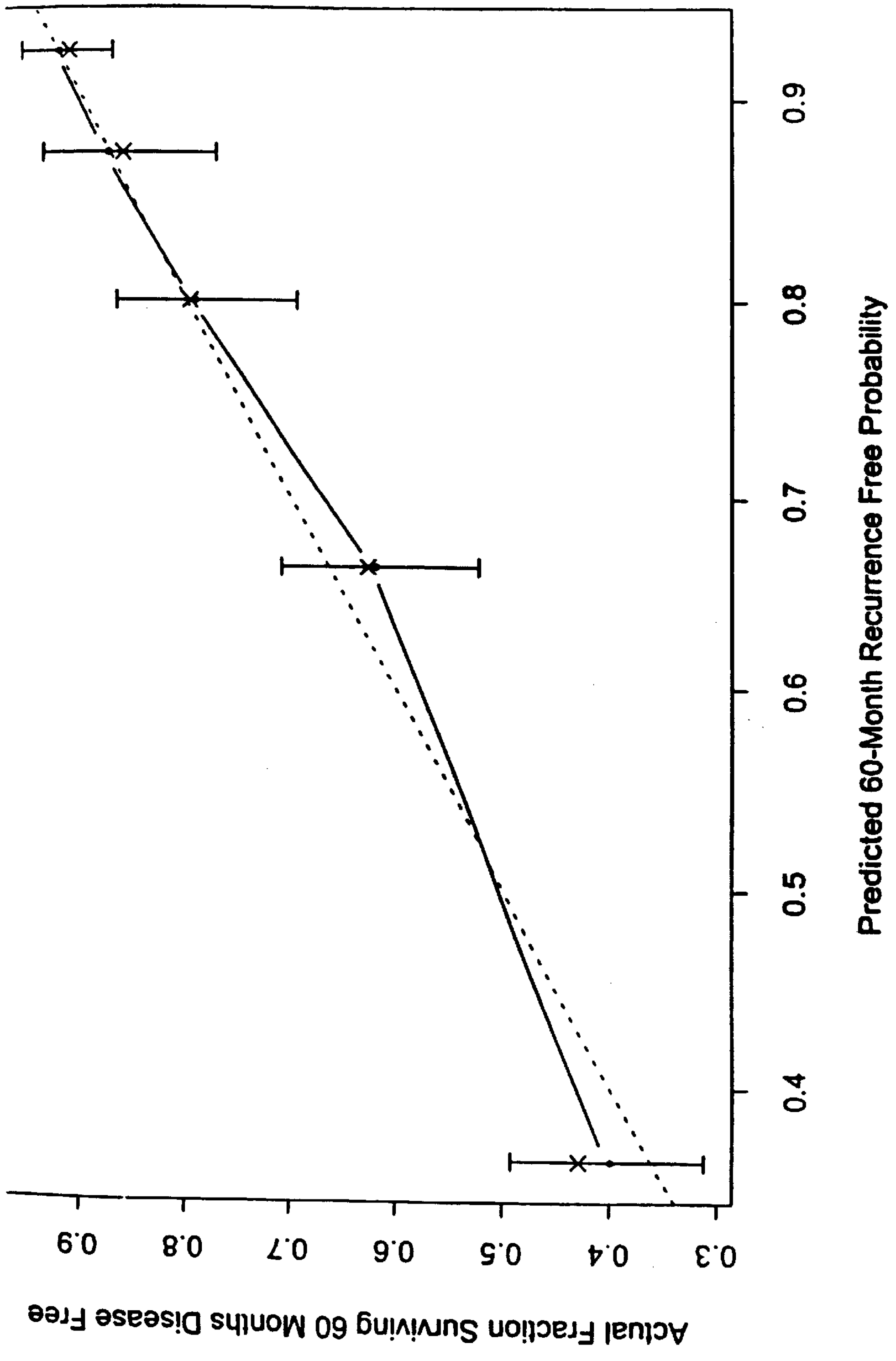
FIG. 3 Comparison of model predictions of FIGS. 2A and 2B with actual outcome.

FIG. 3 illustrates how the model predictions compare with actual outcome of the 983 patients. The x-axis is the nomogram prediction (predicted 60-month recurrence free probability) and the y-axis is the actual freedom from cancer recurrence of the 983 patients (actual fraction surviving 60 months disease free). The dotted line represents the performance of an ideal nomogram, in which predicted outcome perfectly corresponds with actual outcome. The performance of the nomograms of the present invention is plotted as the solid line that connects the dots, corresponding to sub-cohorts (based on predicted risk) within the dataset.

The nomograms' predictions approximate the actual outcomes, since the dots are relatively close to the dotted line. The X's indicate bootstrap-corrected estimates of the predicted freedom from disease recurrence, which are more appropriate estimates of actual freedom from recurrence. Most of the X's are close to the dots, indicating that the nomograms' predictions using the modeled data (the dots) are near that expected with the new data (the X's), though there is some regression to the mean at the extremes. The vertical bars in FIG. 3 indicate 95% confidence intervals based on the bootstrap analysis. In general, the nomograms performances appear to be within 10% of actual outcome, and possibly slightly more accurate at very high levels of predicted probability. There are wider confidence intervals at lower predicted probabilities of recurrence.

Accordingly, one embodiment of the invention is directed to a method for predicting the probability of recurrence of prostatic cancer following radical prostatectomy in a patient diagnosed as having prostatic cancer. This method comprises correlating a selected set of preoperative clinical factors determined for each of a plurality of persons previously diagnosed with prostatic cancer and having been treated by radical prostatectomy with the incidence of recurrence of prostatic cancer for each person of said plurality of persons to generate a functional representation of the correlation, wherein said selected set of preoperative clinical factors comprises pretreatment serum PSA level, combined Gleason grade in the biopsy specimen and clinical stage; and matching an identical set of preoperative clinical factors determined from the patient diagnosed as having prostatic cancer to the functional representation to predict the probability of recurrence of prostatic cancer in the patient following radical prostatectomy. In an alternative embodiment, Gleason sum may be used instead of combined Gleason grade. The terms "correlation," "correlate" and "correlating" as used in connection with the present invention refer to a statistical association between factors and outcome, and may or may not be equivalent to a calculation of a statistical correlation coefficient such as a Pearson correlation coefficient or others.

In a preferred embodiment, the functional representation is a nomogram and the patient is a pre-surgical candidate or someone who has not yet been treated, although the method may also be used in a postoperative situation. In this preferred embodiment, the probability of recurrence of prostatic cancer is a probability of remaining free of prostatic cancer five years following radical prostatectomy. Disease recurrence may be characterized as an increased serum PSA level, preferably greater than or equal to 0.4 ng/mL. Alternatively, disease recurrence may be characterized by positive biopsy, bone scan, or other imaging test or clinical parameter. Recurrence may alternatively be defined as the need for or the application of further treatment for the cancer because of the high probability of subsequent recurrence of the cancer.

In a preferred embodiment, the plurality of persons comprises persons with clinically localized prostate cancer not treated previously by radiotherapy or cryotherapy, who have subsequently undergone radical prostatectomy. This group preferably comprises men diagnosed with prostate cancer between June 1983 and December 1996. In one preferred embodiment, the group comprises men admitted to The Methodist Hospital between June 1983 and December 1996. As will be clear to those of skill in the art, other suitable populations may also be used.

In a preferred embodiment, the nomogram is generated with a Cox proportional hazards regression model. (D. R. Cox, Regression models and life tables (with discussion), Journal of the Royal Statistical Society B34: 187–220, 1972). This method predicts survival-type outcomes using multiple predictor variables. The Cox proportional hazards regression method estimates the probability of reaching a certain end point, such as disease recurrence, over time.

In another embodiment, the nomogram may be generated with a neural network model. (D. E. Rumelhart et al., (eds) Parallel Distributed Processing: Exploration in the Microstructure of Cognition Volume 1. Foundations. Cambridge, Mass.: The MIT Press, 1986). This is a non-linear, feed-forward system of layered neurons which backpropagate prediction errors.

In another embodiment, the nomogram may be generated with a recursive partitioning model. (L. Breiman et al., Classification and Regression Trees. Monterey, Calif.: Wadsworth and Brooks/Cole, 1984). Other models known to those skilled in the art may be alternatively be used.

Another embodiment of this invention is a nomogram for determining a preoperative probability of prostatic cancer recurrence as depicted or represented in FIGS. 2A or 2B. This nomogram may comprise an apparatus for predicting probability of disease recurrence in a patient with prostatic cancer following a radical prostatectomy, wherein the apparatus comprises: a correlation of preoperative clinical factors determined for each of a plurality of persons previously diagnosed with prostatic cancer and having been treated by radical prostatectomy with incidence of recurrence of prostatic cancer for each person of said plurality of persons, wherein said selected set of preoperative clinical factors comprises pretreatment PSA level, combined Gleason grade in the biopsy specimen and clinical stage; and a means for matching an identical set of preoperative clinical factors determined from the patient diagnosed as having prostatic cancer to the correlation to predict the probability of recurrence of prostatic cancer in the patient following radical prostatectomy.

The combined grade in the biopsy specimen (Bx Gleason Grade) is defined as the Gleason grade of the most predominant pattern of prostate cancer present in the biopsy specimen (the primary Gleason grade) plus the second most predominant pattern (secondary Gleason grade), if that pattern comprises at least 5% of the estimated area of the cancer or the histologic sections of the biopsy specimen. For example, a man with a primary Gleason grade of 2 and a secondary Gleason grade of 3 is used in a preferred embodiment of the nomogram as a 2+3, not a 5, which obscures the individual components. Some authors have added the primary and secondary Gleason grades to determine a Gleason "sum," but the preferred embodiments of the preoperative nomograms of the invention illustrated in FIGS. 2A and 2B utilize the primary and secondary Gleason grade designated separately. Nonetheless, in an alternative embodiment of the invention, primary and secondary Gleason grades may be added together and the biopsy Gleason sum used. Note that in the preferred postoperative the embodiment depicted in FIG. 5, specimen Gleason sum is preferably used.

Another embodiment of the invention is directed to a preoperative nomogram which incorporates the three clinical factors of FIGS. 2A or 2B, as well as one or more of the following additional factors: 1) total length of cancer in the biopsy cores; 2) maximum cancer length in a core (Y. Goto et al., J Urol 156 (3):1059–63, 1996); and (3) apoptotic index. Still another embodiment may comprise one or more of the foregoing factors with other routinely determined clinical factors. For example, and not by way of limitation, if available preoperatively, one or more of the factors p53, Ki-67 or p27 may be included. (A. M. F. Stapleton, et al., Cancer 82 (1):168–75, 1998; R. M. Yang et al., J Urol 159 (3):941–5, 1998).

With respect to the total length of cancer in the biopsy cores, it is customary during biopsy of the prostate to take multiple cores systematically representing each region of the prostate. For example, six stratified random cores may be taken from the apex, mid, and base portions of the right and left sides of the prostate. In a preferred embodiment, the total number of millimeters of cancer from the six cores is used. Alternatively, where either more or less than six cores are taken, the percentage of cancerous tissue may be used, calculated as the total number of millimeters of cancer in the cores divided by the total number of millimeters of tissue collected.

With respect to apoptotic index, this may be calculated from the histologic slides of the biopsy specimens as the number of apoptotic bodies divided by the total number of cancer cells counted. (A. M. F. Stapleton et al., Cancer 82 (1):168–175, 1998).

The present invention further comprises a method to predict a preoperative prognosis in a patient comprising matching a patient-specific set of preoperative clinical factors comprising pretreatment PSA level, clinical stage, and combined Gleason grade in the biopsy to the nomogram of FIGS. 2A or 2B and determining the preoperative prognosis of the patient.

The nomogram or functional representation may assume any form, such as a computer program, world-wide-web page, or card, such as a laminated card. Any other suitable representation, picture, depiction or exemplification may be used. In one embodiment, the nomogram comprises a graphic representation of a probability that a patient with prostate cancer will remain free of disease following radical prostatectomy comprising a substrate or solid support, and a set of indicia on the substrate or solid support, the indicia comprising a pretreatment PSA level line, a clinical stage line, a combined Gleason grade in the biopsy line, a points line, a total points line and a predictor line, wherein said pretreatment PSA level line, clinical stage line and combined Gleason grade line each have values on a scale which can be correlated with values on a scale on the points line, and wherein said total points line has values on a scale which may be correlated with values on a scale on the predictor line, such that the value of each of the points correlating with the patient's pretreatment PSA level, combined Gleason grade, and clinical stage can be added together to yield a total points value, and the total points value is correlated with the predictor line to predict the probability of recurrence. The solid support is preferably a laminated card that can be easily carried on a person.

Following radical prostatectomy designed to cure the patient of his cancer, the serum PSA should become undetectable. (A. Stein et al., J Urol 147:942, 1992). Measurable levels of PSA after surgery provide evidence of disease recurrence which may precede detection of local or distant recurrence by many months to years. (A. W. Partin et al., Urol Clin. North Am. 20(4):713–725, 1994). Although clinical experience with elevated serum PSA levels after radical prostatectomy is not yet mature enough to quantify an association with cancer specific mortality, elevated PSA levels are a reasonable measure of the ability of radical prostatectomy to cure a patient with prostate cancer, provided that the follow-up is long enough. This association has been demonstrated for patients with a rising PSA after non-hormonal systemic therapy for advanced prostate cancer, for example, in which men with recurrent cancer evidenced by a rising PSA are more likely to die of prostate cancer earlier than men whose PSA does not rise. (R. Sridhara et al., J Clin Oncol 13:2944–2953, 1995). Serum PSA after radical prostatectomy has been used as an endpoint for treatment efficacy to develop a model which predicts treatment failure. The recurrence decision rule of two PSAs equal to or above 0.4 ng/mL and rising was used as it is relatively safe from indicating false positives, which are particularly undesirable for the patient. It is true that the cutoff choice would affect the nomograms' predicted probabilities, so the results of the nomograms may be somewhat different than the actual outcome of patients at centers which use a different PSA cutoff rule. Furthermore, using a particular level of PSA as an event indicates that PSA follow-up data are interval-censored (occurring between two time points) (F. J. Dorey et al., Stats in Med 12:1589–1603, 1993) rather than right-censored (simply unknown after last follow-up), as modeled. However, adjuvant treatment decisions are often based on observed PSA recurrences, so that this endpoint is more useful clinically than the true PSA recurrence time.

The interest in PSA recurrence as an endpoint of a preoperative model motivated the survival-type analysis used in the preoperative nomograms of the present invention. In addition to serving as a prognostic tool, the nomograms in FIGS. 2A or 2B are useful for interpreting the underlying Cox model. PSA is influential across its spectrum, though patients with a very high PSA are rarely considered good candidates for surgery. The nomograms assign many points for cT3a and high grade disease, which is consistent with the clinical expectations of most physicians. The Cox model coefficients, and therefore the resulting nomograms, look very similar when only the complete records (without imputing) are modeled.

The preoperative nomograms of the present invention were based on patients who received radical prostatectomy, so they are most applicable to patients who otherwise appear to be candidates for surgery, rather than all patients diagnosed with prostate cancer. Given the selection by both patient and urologist (e.g., biopsy or serum criteria), either nomogram can be applied as a last step in the decision making process after the patient has decided upon radical retropubic prostatectomy as his treatment choice. The nomograms are not necessarily applicable for changing the mind of the patient who has decided against radical retropubic prostatectomy since his recurrence probability is not known; rather, they are designed to be used for revisiting the choice of surgery.

One way to apply either nomogram is to say, "Mr. X, if we had 100 men exactly like you, we would expect between <lower confidence limit> and <upper confidence limit> would remain free of their disease following radical prostatectomy for 5 years, assuming they did not die of something else first, and recurrence after 5 years is rare."

The nomograms are useful although they may not always predict with perfect accuracy. For example, with regard to the nomograms of FIGS. 2A and 2B, the area under the ROC curve on the validation sample was 0.79, while the bootstrap corrected estimate on the original sample was 0.74, which may be overly conservative in this case. Although the difference between the two may not be statistically significant, it is somewhat odd for the validation sample performance to be higher than even the uncorrected training sample performance (0.76), so true discriminatory power may be closer to 0.74 than 0.79 since the validation sample was small with few recurrences. Also, with respect to accuracy, the confidence intervals at the various predicted probabilities of recurrence (FIG. 3) are somewhat wide, at some levels as much as +/−10%. At the individual patient level, this level of error is difficult to interpret since a single patient will either recur or not.

The cohort of patients in the original sample were all treated by a single surgeon and all data came from a single institution, which may affect generalizability to other urologists and institutions. Most of the patients were Caucasian, and while race has not been an independent predictor of recurrence in the data, others have found a postoperative racial effect, which may limit applicability for non-Caucasians. (J. W. Moul et al., J Urol. 155:1667–1673, 1996). Validation was performed on the data from different surgeons and accrued more recently than modeled in the nomogram. Application of the nomogram assumes that the effectiveness of the intervention (RRP) is similar at other institutions or in the community.

In addition to assisting the patient and physician in selecting an appropriate course of therapy, the nomograms of the present invention should also prove useful in clinical trials to identify patients appropriate for a trial, to quantify the expected benefit relative to baseline risk, to verify the effectiveness of randomization, to reduce the sample size requirements, and to facilitate comparisons across studies.

b. Embodiments Including Postoperative Variables

In addition to the various embodiments of the preoperative nomograms and method of using the nomograms discussed above, the present invention is also directed toward postoperative nomograms and methods of utilizing these nomograms to predict probability of disease recurrence following radical prostatectomy. This prognosis may be utilized, among other reasons, to determine the usefulness of adjuvant therapy in a patient following radical prostatectomy.

Accordingly, further embodiments of the present invention include a nomogram which incorporates clinical and pathologic factors, including postoperative factors, to predict probability of cancer recurrence after radical prostatectomy for clinically localized prostatic cancer. This nomogram predicts probability of disease recurrence using clinical and pathologic factors for patients who have received radical prostatectomy to treat clinically localized prostate cancer.

Using a Cox proportional hazards regression model, preoperative PSA and pathologic parameters were used to predict PSA or clinical recurrence in 996 men with clinical stage T1a-T3c N0-1M0 prostate cancer who were treated by radical prostatectomy by a single surgeon at The Methodist Hospital in Houston, Tex. Predictive factors included preoperative PSA level, specimen Gleason sum, prostatic capsular invasion level, surgical margin status, presence of seminal vesicle invasion, and lymph node status. Treatment failure was recorded when there was either clinical evidence of disease recurrence, a rising serum prostate specific antigen level (two measurements of 0.4 ng/mL or greater), or initiation of adjuvant therapy.

The 996 men modeled were selected from a group of 1145 patients. Specifically, 1145 patients who were treated with radical retropubic prostatectomy by a single surgeon during the period from June 1983 through June 1997 at The Methodist Hospital were potential candidates for this analysis. Pelvic lymph node dissections were performed on all men. Radical prostatectomy was aborted in 32 of the 58 patients who were found to have nodal metastases on frozen section analysis during the operation; these 32 men were excluded from the analysis. Also excluded were men treated with definitive radiotherapy (N=56), hormonal therapy (N=43), cryotherapy (N=3), or other radiotherapy (N=3) prior to the radical procedure. No disease follow-up information was available for 12 men, and they were also excluded. This left 996 men for analysis. Clinical stages were as follows: T1a (3.2%), T1b (4.3%), T1c (16.5%), T2a (27.1%), T2b (24.1%), T2c (18.5%), T3a (5.4%), T3b (0.1%), and T3c (0.89%). The final pathologic stage, determined by the study pathologist after the surgical specimen was sectioned serially at 5 mm intervals (M. Ohori et al., Cancer 74:104–114, 1994) was distributed as follows: pT2N0, confined to the prostate (55.8%); pT3aN0, extraprostatic extension, either focal or established (27.2%); pT3bN0, seminal vesicle involvement (9.1%); and pT2-3N1, pelvic lymph node metastasis (7.1%). Surgical margins were positive (ink touching cancer cells at the edge of the specimen) in 143 (14%) of the patients (M. Ohori et al., J Urol 154:1818–1824, 1995).

The level of prostate capsular invasion (PCI) with respect to the stroma of the prostate, prostatic capsule, and periprostatic soft tissue was classified as follows (T. M. Wheeler, Urol Clin North Am 16:523, 1989; Shenkenberg, Rice L. et al., Cancer 49:1924, 1982):

Confined:

Level 0 (L0) Tumor confined to prostatic stroma within the boundary of normal prostatic acini.

Level 1 (L1) Tumor confined to prostatic stroma, but outside the boundary of normal prostatic acini.

Level 2 (L2) Tumor confined to the prostate but within a layer more fibrous than muscular (capsule). Anteriorly and at the apex where "capsule" does not exist, the distinction between L1 and L2 is somewhat arbitrary.

Non-Confined:

Level 3 (L3) Tumor invasive into the periprostatic adipose tissue or smooth muscle of bladder neck.

Level 3 focal (L3F) Tumor outside the prostate to a depth of less than one high-power field on no more than two separate sections.

Level 3 established (L3E) Any amount of extraprostatic tumor more than L3F.

Seminal vesicle involvement or invasion was defined as cancer within the muscular coat of the seminal vesicle, not simply tumor in the fat adjacent to the seminal vesicle (M. Ohori et al., Am J Surg Pathol 17(12): 1252–1261, 1993).

The median age of all patients was 63 years (range, 38–81 years), and 88% of the patients were Caucasian. For predictors of recurrence, selected preoperative serum PSA was selected in addition to the following routinely performed pathologic variables: Gleason sum in the surgical specimen ("Gleason sum"), prostatic capsular invasion level, surgical margin status, seminal vesicle invasion, and lymph node status. Biopsy Gleason grade and clinical stage were not included as predictor variables since they are both preoperative estimates of their pathologic counter parts, which were included as predictors. Preoperative PSA was measured by the Hybritech Tandem-R assay (Hybritech, Inc., San Diego, Calif.). In 64 patients (6.4%) treated before the PSA assay became available at the subject institution, no preoperative PSA level was determined. All prostates were totally embedded and sectioned by the whole-mount technique. A single pathologist measured the pathologic variables. In the interest of a parsimonious model, recently developed markers with less demonstrated predictive value (e.g., percent free PSA) were not included in the analysis. Missing values for PSA (N=64), prostatic capsular invasion (N=9), Gleason sum (N=4), surgical margins (N=4), seminal vesicle invasion (N=3), and lymph node status (N=3) were imputed with regression models (F. E. Harrell. Transcan: An S-Plus function. Program available from statlib@lib.stat.cmu.edu. Send e-mail 'send transcan from S,' 1995) containing all of the predictor variables to estimate the value of the missing predictor variable without reference to the outcome (PSA recurrence). Imputing a missing value is generally preferred to deleting a patient's entire medical record, so that the maximum information is utilized and the bias that may result from a deleted case can be avoided (F. E. Harrell et al., Stats Med 15:361–387, 1996). However, for comparison, a dataset consisting of only complete records was modeled as well. The descriptive statistics of all predictor variables after imputing appear in Table 4.

TABLE 4

Descriptive statistics of the predictor variables for 996 patients undergoing radical retropubic prostatectomy after missing values were imputed. "N" refers to the number of patients in each catergory. "%" refers to the percent of all patients falling within the noted category.

| | N | % |
|---|---|---|
| Gleason Sum | | |
| 3 | 2 | 0.2 |
| 4 | 5 | 0.5 |
| 5 | 106 | 10.6 |
| 6 | 350 | 35.1 |
| 7 | 454 | 45.6 |
| 8 | 61 | 6.1 |
| 9 | 14 | 1.4 |
| 10 | 4 | 0.4 |
| Prostatic Capsular Invasion | | |
| None | 184 | 18.5 |
| Invading Capsule | 396 | 39.8 |
| Focal | 152 | 15.3 |
| Established | 264 | 26.5 |
| Surgical Margins | | |
| Neg | 853 | 86.5 |
| Pos | 143 | 13.5 |
| Seminal Vesicle Invasion | | |
| No | 862 | 86.5 |
| Yes | 134 | 13.5 |
| Lymph Nodes | | |
| Neg | 925 | 92.9 |
| Pos | 71 | 7.1 |

| Preoperative PSA (ng/ml) | |
|---|---|
| Min | 0.1 |
| Median | 7.1 |
| Mean | 10.4 |
| Max | 100.0 |

The time of treatment failure was defined as either the earliest date that the postoperative serum PSA level rose to 0.4 ng/mL or higher (N=124, confirmed by a second PSA higher than the first by any amount), or the earliest date of clinical evidence of cancer recurrence in patients with an undetectable PSA (N=4) or no PSA result (N=27) who developed recurrence before PSA was routinely measured. Patients who were treated with hormonal therapy (N=6) or radiotherapy (N=26) after surgery but before documented recurrence were treated as failures at the time of second therapy, due to interest in predicting who would eventually need second treatment for their cancer and the fact that adjuvant therapy may mask the appearance of measurable PSA in the serum. An additional two men, one of whom was treated before PSA was available as a clinical test, were reported as dead of prostate cancer with no available documentation to support evidence of recurrence prior to death, and these patients were considered treatment failures.

A separate sample for validation was composed of 322 patients with prostate cancer who had been treated by any one of five other surgeons at The Methodist Hospital. These were the patients with complete records only, and no values were imputed. As with the modeling sample, preoperative PSA was measured with the Hybritech assay immediately before biopsy (if available) or before radical prostatectomy, and pathologic variables were measured by a single pathologist. Each individual surgeon assigned the clinical staging for his/her patients. Patients were accrued from October 1990 through June 1997. All patients from both samples came from the Specialized Program of Research Excellence (SPORE) Prostate Information System database (Baylor College of Medicine).

Estimates of the probability of remaining free from recurrence were calculated with the Kaplan-Meier method. Multivariable analysis was conducted with Cox proportional hazards regression. The proportional hazards assumption was verified by tests of correlations with time and examination of residual plots. PSA had a skewed distribution and suspected nonlinear effect, so it was modeled as a restricted cubic spline (F. E. Harrell et al., Stats Med 15:361–387, 1996) of its log. Similarly, Gleason sum was suspected to be nonlinear and also modeled with a restricted cubic spline function. Prostate cancer within the confines of the glandular prostate or in the prostatic stroma but beyond the limit of the normal acini had to be combined as "None" due to no patients in first group experiencing recurrence, which would prohibit convergence of the Cox algorithm. All decisions with respect to the coding of the nomogram variables were made prior to modeling. This Cox model was the basis for a nomogram.

Validation of the postoperative nomogram contained three components. First, the nomogram was subjected to bootstrapping, with 200 re-samples, as a means of calculating a relatively unbiased measure of its ability to discriminate among patients, as quantified by the area under the receiver operating characteristic curve (J. A. Hanley et al., Radiology 143:29–36, 1982). With censored data, the receiver operating characteristic calculation (F. E. Harrell et al., Stats Med 15:361–387, 1996) was slightly modified from its normal method. Nonetheless, its interpretation was similar. The area under the receiver operating characteristic curve was the probability that, given two randomly drawn patients, the patient who recurred first had a higher probability of recurrence. This calculation assumed that the patient with the shorter follow-up recurred. If both patients recurred at the same time, or the non-recurrent patient had shorter follow-up, the probability did not apply to that pair of patients. The second validation component was to compare predicted probability of recurrence versus actual recurrence (i.e., nomogram calibration) on the 996 patients, again using 200 bootstrap re-samples to reduce overfit bias, which would overstate the accuracy of the nomogram. Finally, the third validation component was simply to apply the nomogram to the 322 patients not included in the modeling sample. For these patients, their predicted probability of recurrence was compared with actual follow-up, and the area under the receiver operating characteristic curve for these men was calculated. All statistical analyses were performed using S-Plus software (PC Version 4.0, Redmond Wash.) with additional functions (called Design) (F. E. Harrell, FE. Design: S-Plus function for biostatistical/epidemiologic modeling, testing, estimation, validation, graphics, prediction, and typesetting by storing enhanced model design attributes in the fit. 1994. Programs available from statlib@lib.stat.cmu.edu) added. All P values resulted from use of two-sided statistical tests.

Figure 4:
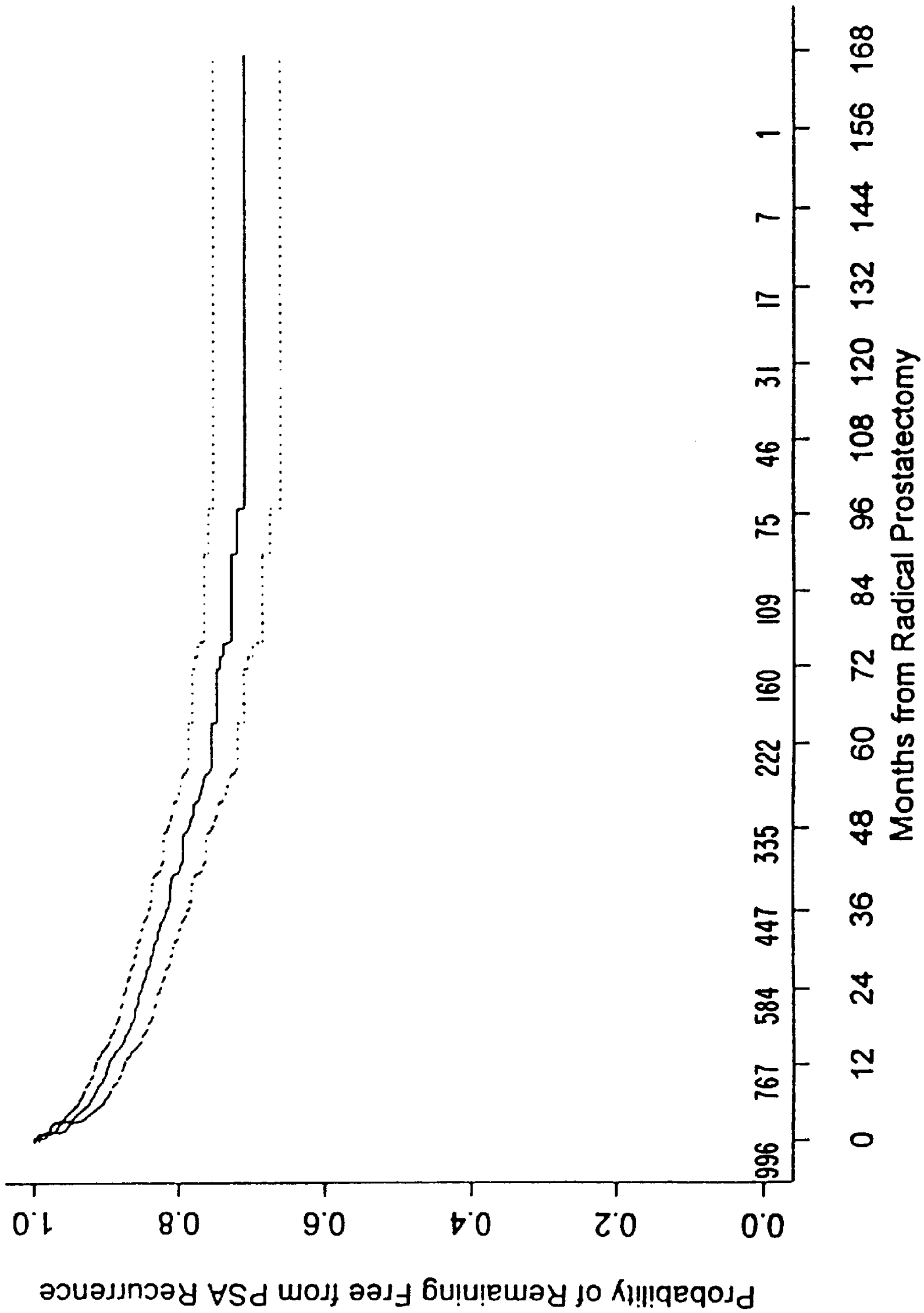
FIG. 4 Graph of overall recurrence-free probabilities following radical prostatectomy for the postoperative nomogram of FIG. 5.

Of the 996 patients available for analysis, 189 had evidence of recurrence of prostate cancer following radical prostatectomy. For patients without disease recurrence, median follow-up was 37 months (range, 1 to 168 months). There were 222 patients with at least 60 months disease-free follow-up, 109 with 84 months disease-free follow-up, and 31 patients with at least 120 months disease-free follow-up. Overall recurrence-free probability for these patients with clinical stage T1a-T3c N0-1M0 prostate cancer was 75% (95% CI=72%–79%) at 5 years, 73% (95% CI=68%–76%) at 7 years, and 71% (95% CI=66%–75%) at years. FIG. 4 depicts the Kaplan-Meier estimates of disease free probability with 95% confidence intervals for the 996 patients treated with radical prostatectomy during the period from June 1983 through June 1997. The x-axis depicts months from radical prostatectomy and the y-axis depicts the probability of remaining free from PSA recurrence. Numbers above the months indicate patients at risk for recurrence. Recurrence beyond the 7-year point is rare in this series (O. Dillioglugil et al., Urol 50:93–99, 1997). No recurrences were observed later than 97 months, but the tail of the curve is retained in FIG. 4 to illustrate follow-up. In the multivariable model, all variables were associated with recurrence ($P<0.01$ for each).

Figure 5:
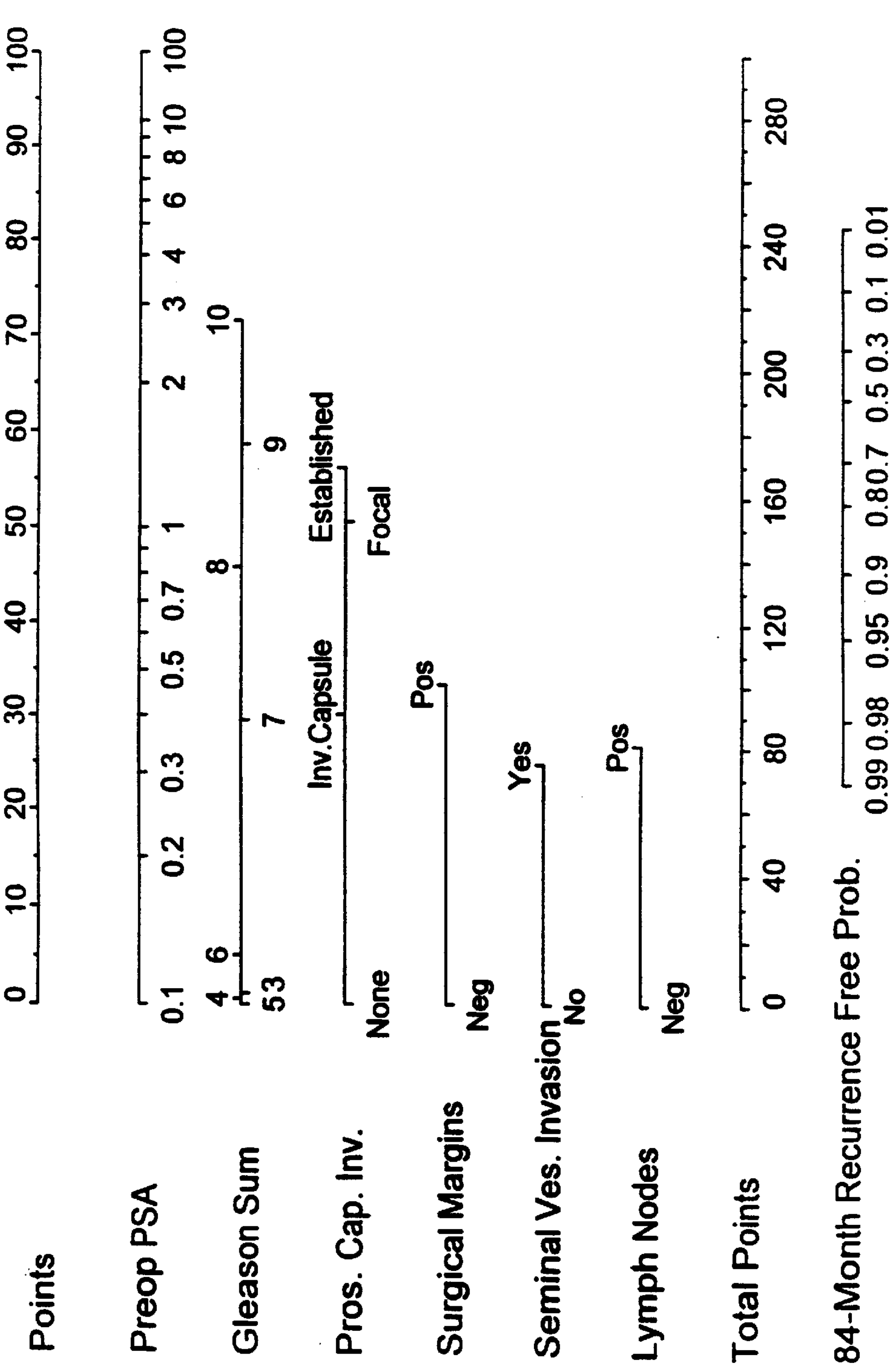
FIG. 5 A third nomogram useful for the postoperative assessment of probability of cancer recurrence following radical prostatectomy.

A nomogram incorporating each of these clinical predictors was constructed based on the Cox model and appears in FIG. 5. The nomogram is used by first locating a patient's position on each predictor variable scale (PSA through lymph node status). Each scale position has corresponding prognostic points (top axis). For example, a PSA of 4 contributes approximately 78 points; this is determined by comparing the location of the 4 value on the "PSA" axis to the "Points" scale above and drawing a vertical line between the 2 axes. The point values for all predictor variables are determined in a similar manner and are then summed to arrive at a Total Points value. This value is plotted on the Total Points axis (second from the bottom). A vertical line drawn from the Total Points axis straight down to the 84-Month PSA Progression-Free Survival axis will indicate the patient's probability of remaining free from cancer recurrence for 7 years assuming he remains alive.

The nomogram of FIG. 5 was evaluated for its ability to discriminate among patients' risk of recurrence. This was measured as the area under the receiver operating characteristic curve for censored data. This area represents the probability that, when two patients are randomly selected, the patient with the worse prognosis (from the nomogram) will recur before the other patient. This measure can range from 0.5 (a coin toss) to 1.0 (perfect ability to discriminate). Using the original 996 patients who were modeled for the nomogram, the area was calculated to be 0.88.

To derive an estimate of expected performance of the nomogram against new patients, bootstrapping was performed, a statistical method in which sampling, nomogram building, and nomogram evaluation are repeated a large number of times (B. Efron et al., An Introduction to the Bootstrap. New York, N.Y., Chapman and Hall, 1993). This approach simulates the presentation of new patients to the nomogram. With the use of bootstrapping, performance of the nomogram was essentially unchanged, with an area under the receiver operating characteristic curve of 0.88. A decrease in accuracy was expected. However, finding no decrease suggests that the nomogram should perform with similar accuracy in additional, similar patient populations.

Figure 6:
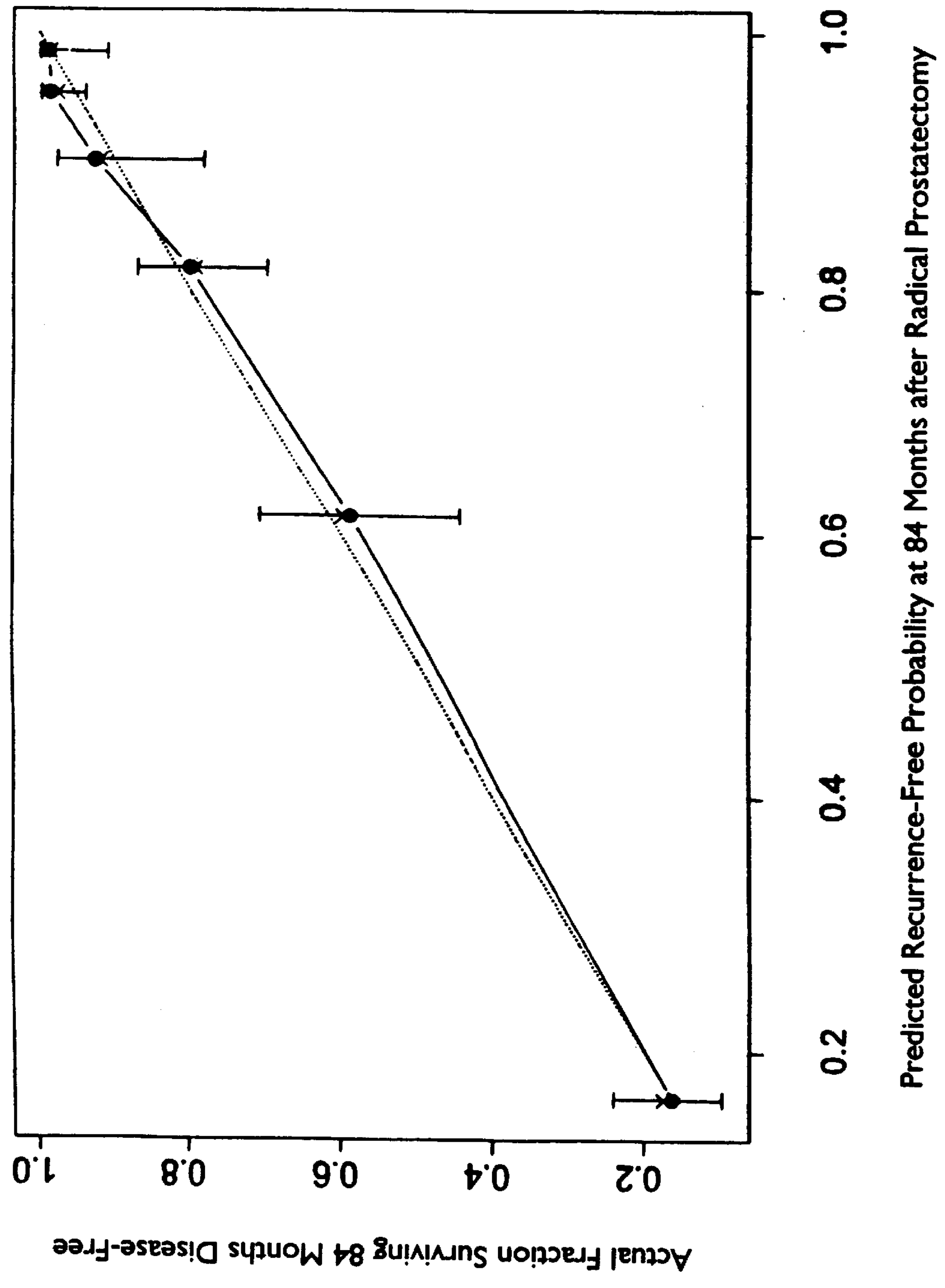
FIG. 6 Comparison of model predictions of FIG. 5 with actual outcome.

FIG. 6 is a calibration of the nomogram of FIG. 5 which illustrates how the predictions from the nomogram compare with actual outcomes for the 996 patients. The x-axis is the prediction calculated with use of the nomogram (predicted recurrence-free probability at 84 months after radical prostatectomy) and the y-axis is the actual freedom from cancer recurrence for the patients (actual fraction surviving 84 months disease-free). The dashed line represents the performance of an ideal nomogram, in which predicted outcome perfectly corresponds with actual outcome. The post-operative nomogram performance is plotted as the solid line that connects the dots, corresponding to sub-cohorts (based on predicted risk) within the dataset. Because the dots are relatively close to the dashed line, the predictions calculated with use of the nomogram approximate the actual outcomes. The X's indicate bootstrap-corrected estimates of the predicted freedom from disease recurrence, which are more appropriate estimates of actual freedom from recurrence. Most of the X's are very close to the dots, indicating that the predictions based on use of the nomogram and modeled data (the dots) are near that expected from use of the new data (the X's). The vertical bars in FIG. 6 indicate 95% confidence intervals based on the bootstrap analysis. In general, the performance of the nomogram appears to be within 10% of actual outcome, and possibly slightly more accurate at very high levels of predicted probability.

As a final method of validation, the probability of 7-year recurrence was predicted for the separate sample of 322 patients. Of these men, 20 had disease recurrence. The predictions made with use of the nomogram were compared with actual outcomes, and the area under the receiver operating characteristic curve was calculated and found to be 0.89.

The disadvantage of the probability approach of the present invention over the previously-used relative risk approach is that when reporting a probability the point in time must be specified. Too early of a time point (e.g., probability of recurring within 2 years) loses clinical usefulness by being inconclusive. Too late of a time point has the disadvantage of potentially being estimated when few patients in the series are at risk that may result in low precision. In the present study, a time point of 84 months was selected in attempt to balance these concerns. Recurrence by PSA is very rare after 84 months, which provides support for judging whether surgery is effective, yet 109 patients remained at risk for recurrence in the present model at 84 months, such that the estimate of the probability at that time may remain reasonably stable.

The present invention differs from those previously published in its methods of validation and assessment. The previous work by Partin and Bauer illustrate the extreme difficulty in validating a survival model. They both produced Kaplan-Meier estimates for the risk strata using validation cohorts, but probably due to small sizes of the cohorts, neither study was able to report all pairwise differences among the strata (i.e., each strata being different from each other strata). The present invention enhances the efficiency of validation and assessment in two ways. First, bootstrapping was employed (B. Efron et al., An Introduction to the Bootstrap. New York, N.Y., Chapman and Hall, 1993) so that each patient could legitimately be used for both model development and model assessment. This more fully utilizes the dataset at hand than does the approach of dividing up the dataset into strata. Second, an overall measure of the ability of the model of the present invention to discriminate among the individual patient's risk of recurrence was reported. In this manner, one can avoid having to form strata that combine patients who are at varying levels of risk into the same risk group. Instead, the discrimination measure of the present invention (area under the receiver operating characteristic curve for censored data) compares each pair of patients and quantifies the degree to which the model was able to rank those patients. Moreover, the present invention bootstraps the discrimination measure to obtain a reasonable estimate of expected discrimination ability on future data. As two further points of difference with previous studies, the present invention includes patients with clinical stage T3b and T3c disease and utilizes relatively large (N=996 for derivation and N=322 for validation) datasets.

In addition to potentially comforting the patient who is at low probability of recurring, the nomogram of FIG. 5 also has several important uses involving clinical trials. First, it is useful in identifying patients who are appropriate for a clinical trial. The nomogram provides the patient and clinician with the patient's baseline probability of recurrence and together they can decide whether adjuvant therapy is necessary and worth the side effects. Second, as an extension to the first use, the nomogram is potentially able to quantify the expected benefit relative to the baseline risk. A patient at very low risk for recurrence may not have much to gain from a new treatment (R. M. Califf et al., American Heart J 133(6): 630–639, 1992; W. A. Knaus et al., JAMA 270(10):1233–1241, 1993; W. A. Knaus et al., Theor Surg 9:20–27, 1994). In conjunction with the expected efficacy of adjuvant therapy, the nomogram allows quantification of this potential net gain. This is useful even after a clinical trial demonstrates superiority of one treatment over another. The reason for this is that the degree of benefit could be highly variable among patients who are at different baseline risks (R. M. Califf et al., American Heart J 133(6):630–639, 1992). Third, the nomogram can be used to verify the effectiveness of randomization (W. A. Knaus et al., JAMA 270(10):1233–1241, 1993; W. A. Knaus et al., Theor Surg 9:20–27, 1994; W. A. Knaus et al., Crit Care Med 24(1): 46–56, 1996). Treatment arms should have very similar average baseline risks. Fourth, the nomogram may make it possible to reduce the sample sizes of clinical trials for adjuvant therapies (W. A. Knaus et al., Theor Surg 9:20–27, 1994; W. A. Knaus et al., Crit Care Med 24(1): 46–56, 1996). A typical multivariable analysis consumes several degrees of freedom to adjust for potential effects of confounding variables. In other words, part of the sample size requirement for a new trial is associated with estimating the effect of the new therapy, and part is associated with adjusting for the effects of the patient's baseline variables. By collapsing the effects of several baseline variables into an overall recurrence risk (which consumes fewer degrees of freedom than the individual components), a smaller sample is needed because of a smaller demand placed on the trial data to be able to adjust for baseline differences in the treatment arms. Fifth, a uniform method of patient description would help to facilitate comparisons across studies (W. A. Knaus et al., Crit Care Med 24(1): 46–56, 1996). Typical studies report univariable tables of each baseline variable that do not illustrate potential differences in their joint distribution, which the nomogram would consider.

Other possible uses of the nomogram include facilitating the search for a new marker of eventual recurrence following surgery for prostate cancer. Analogous to the clinical trial use above, the sample size requirements to evaluate whether a new marker contributes to the prognostic ability of existing markers are reduced. The nomogram collapses the ability of the previous markers into an overall risk measure which requires a smaller sample size for adjustment, which in turn reduces the overall sample size requirement and thus the number of patients who need to have their new marker measured. Another major use of the nomogram is related to the desire to provide cost effective treatment for society (W. A. Knaus et al., JAMA 270(10):1233–1241, 1993; W. A. Knaus et al., Science 254:389–394, 1991). By quantifying the expected benefit a patient is to receive from a potential treatment and incorporating its cost, a calculation is facilitated as to whether a treatment's expected benefit is worth its expected cost. The purpose here is not to deny the treatment to the patient but instead decide whether the treatment is cost effective from society's point of view (i.e., whether it should be reimbursable).

In addition to serving as a prognostic tool, the nomogram in FIG. 5 is useful for interpreting the underlying Cox model. For example, it appears that PSA is very influential across its spectrum. Also, the nomogram assigns points for the levels of prostatic capsular invasion consistent with degree of tumor spread. Similarly, positive margins, seminal vesicle invasion, and positive lymph nodes each increase the number of points the patient receives towards recurrence. However, the point assignment for Gleason sum appears counter-intuitive (e.g., sum=3 worse than sum=4 worse than sum=5), but these differences reflect variations in coefficient estimates and are not statistically significant (two-sided P>0.05). Furthermore, it is important to consider possible changes in other variables (e.g., PSA) when comparing points across levels of a single variable (e.g., seminal vesicle invasion) since patients who differ on one axis are likely to differ on another axis and not be held constant which the eye assumes when comparing across axes. The Cox model coefficients, and therefore the resulting nomogram, look very similar when only the complete records (without imputing) are modeled (data not shown).

The postoperative nomogram of FIG. 5 has certain limitations. The area under the receiver operating characteristic curve on the validation sample was 0.89, while the bootstrap corrected estimate on the original sample was 0.88. Thus, in 11%–12% of patient pairs, the patient with the better prognosis actually recurred first. Also, with respect to accuracy, the confidence intervals at the various predicted probabilities of recurrence (FIG. 6) are somewhat wide, at some levels as much as plus or minus 10%. For the individual patient, this level of error is difficult to interpret since a single patient will either recur or not. One way to apply the nomogram is to say, "Mr. X, if we had 100 men exactly like you, we would expect between <lower confidence limit> and <upper confidence limit> to remain free of their disease for 7 years, assuming they did not die of something else first, and recurrence by PSA after 7 years is rare."

Data from a single surgeon was modeled, and all data came from the same institution. Most of the patients were Caucasian, although others have found no effect of race in multivariable recurrence models prior to variable selection after controlling for fewer pathologic criteria [P=0.083 in J. W. Moul et al., J Urol 155:1667–1673, 1996, P=0.054 in J. J. Bauer et al., Cancer 79(5):952–962, 1997, not shown in J. J. Bauer et al., J. Urol 159:929–933, 1998]. Although the validation was performed on data that had been obtained from different surgeons and accrued more recently than the data in the nomogram, there may be subtle commonalties among them. In addition, a single expert pathologist performed all pathological assessment. The accuracy of the nomogram in the wider medical community assumes comparable grading accuracy by other pathologists. Further, the applicability of the nomogram assumes that the probability of cancer control after radical prostatectomy is similar when surgeons at other institutions perform the surgery. In fact, there may be substantial variations in outcome, partially due to technical aspects of the operation as measured, for example, by the rate of positive surgical margins.

Nonetheless, the nomogram of FIG. 5 that allows one to predict, from the serum PSA, level of prostatic capsular invasion, specimen Gleason sum, surgical margin status, seminal vesicle invasion, and lymph node status, the probability of cancer recurrence after radical prostatectomy for prostate cancer. The nomogram combines readily available factors and may assist the physician and patient in deciding whether or not adjuvant therapy is an acceptable treatment option. It may also be useful in the design of adjuvant treatment protocols.

Accordingly, one embodiment of this invention is directed to a postoperative method for predicting probability of recurrence of prostatic cancer in a patient who has previously undergone a radical prostatectomy comprising: correlating a selected set of clinical and pathological factors determined for each of a plurality of persons previously diagnosed with prostatic cancer with the incidence of recurrence of prostatic cancer for each person of said plurality to generate a functional representation of the correlation, wherein said selected set of factors comprises one or more of the following: (1) preoperative PSA level; (2) specimen Gleason sum; (3) prostatic capsular invasion level; (4) surgical margin status; (5) presence of seminal vesicle invasion; and (6) lymph node status, wherein said plurality of persons comprises men having undergone radical prostatectomy; and matching an identical set of factors determined from the patient to the functional representation to predict the probability of recurrence of prostatic cancer for the patient.

In a preferred embodiment, the plurality of persons comprises men diagnosed with prostatic cancer and treated with radical retropubic prostatectomy. Preferably, these men underwent surgery between June 1983 and June 1997 at The Methodist Hospital. As will be clear to one of skill in the art, other suitable populations may be used.

In a preferred postoperative embodiment, surgical margin status is reported as negative or positive. Alternatively, surgical margin status may be reported as negative, close or positive. Prostatic capsular invasion level is preferably reported as none, invading the capsule, focal or established.

Seminal vesicle involvement or invasion is preferably reported as yes or no. Alternatively, it may be ranked as positive or negative, or absent or present. If present, seminal vesicle involvement can be alternatively classified by level as Types I, II, I+II, or III (M. Ohori et al., Am J Surg Pathol 17:1252–1261, 1993). In yet another embodiment, seminal vesicle invasion, if present, may be alternatively ranked by level as type I, II, or III (T. M. Wheeler, Urol Clin North Am 16:623–634, 1989; M. Ohori et al., Am J Surg Pathol 17:1252–1261, 1993). Lymph node status is preferably recorded as either positive or negative. In alternative embodiments, one or more subgroups of any one or more of these factors may be excluded.

In yet another embodiment, the selected set of clinical and pathological factors may further include one or more of the following: the volume of cancer (total tumor volume), the zone of the prostate where the tumor is found (zone of location of the cancer), level of extraprostatic extension, p53, Ki-67, p27, DNA ploidy status, clinical stage, lymphovascular invasion, and other routinely determined pathological factors. (D. R. Greene et al., J Urol 146:1069–1076, 1991; D. R. Greene et al., Campbell's Urology, vol. 1, 6th ed, W. B. Saunders Co., 1992; M. Ohori et al., Prostate 23 (4):271–281, 1993; A. M. F. Stapleton, et al., Cancer 82 (1):168–75, 1998; R. M. Yang et al., J Urol 159 (3):941–5, 1998 ).

Level of extraprostatic extension may be evaluated as negative, level 1, level 2, level 3 focal, or level 3 established (Stamey et al., J Urol 139:1235–1241, 1998; Rosen et al., J Urol 148:331–337, 1992). Alternatively, level of extraprostatic extension may be evaluated as negative, level 1, level 2 or level 3 focal. Alternatively, level of extraprostatic extension may be evaluated as level 0 or 1 (no invasion of the capsule or extension outside of the prostate), level 2 (invasion into but not through the capsule), level 3F (focal microscopic extension through the capsule comprising no more than two high power fields on all histologic sections), or level 3E (established extension through the capsule more extensive than level 3F) (T. M. Wheeler et al., Hum Pathol 29(8), 1998, in press; M. Ohori et al., Am J Surg Pathol 17:1252–1261, 1993; D. R. Greene et al., J Urol 146:1069–1076, 1991; D. R. Greene et al., Campbell's Urology, vol. 1, 6th ed. W.B. Saunders Co. 342–393, 1992; D. R. Greene et al., Br. J Urol. 68:499–509, 1991; M. Ohori et al., Prostate 23(4):271–281, 1993).

The probability of recurrence of prostate cancer of the preferred embodiment is defined as the probability of remaining free of prostatic cancer seven years following radical prostatectomy. Recurrence may be characterized as an increased serum PSA level or as positive biopsy, bone scan, or other suitable imaging test or clinical parameter. Alternatively recurrence may be characterized as a positive biopsy, bone scan or the initiation or application of further treatment for prostate cancer because of the high probability of subsequent recurrence of the cancer.

In a preferred embodiment, the functional representation is a nomogram. The nomogram may be generated with a Cox proportional hazards regression model. (D. R. Cox, Regression models and life tables (with discussion), Journal of the Royal Statistical Society B34: 187–220, 1972). Alternatively, the nomogram may be generated with a neural network model. (D. E. Rumelhart et al., Parallel Distributed Processing: Exploration in the Microstructure of Cognition Volume 1. Foundations. Cambridge, Mass.: The MIT Press, 1986). In still another embodiment, the nomogram is generated with a recursive partitioning model. (L. Breiman et al., Classification and Regression Trees. Monterey, Calif.: Wadsworth and Brooks/Cole, 1984). Other models known to those skilled in the art may alternatively be used.

Still another embodiment of the invention is directed to a nomogram for determining a postoperative probability of prostatic cancer recurrence as depicted or represented in FIG. 5.

Another embodiment of the invention is directed to a method to predict a postoperative prognosis in a patient following radical prostatectomy, comprising matching a patient-specific set of clinical and pathological factors comprising the patient's preoperative PSA level, specimen Gleason sum, prostatic capsular invasion level, surgical margin status, presence of seminal vesicle invasion, and lymph node status to the nomogram depicted in FIG. 5 and determining the prognosis of the patient.

Still another embodiment of the invention is directed to a method for determining a need for an adjuvant therapy in a patient following radical prostatectomy comprising the steps of: determining a set of clinical and pathological factors on the patient, the set of factors comprising the patient's preoperative PSA level, specimen Gleason sum, prostatic capsular invasion level, surgical margin status, presence of seminal vesicle invasion, and lymph node status; and matching the set of factors to the nomogram depicted in FIG. 5 to determine whether the adjuvant therapy is needed in view of the probability of recurrence. The adjuvant therapy may comprise radiotherapy, chemotherapy, hormonal therapy (such as anti-androgen hormonal therapy), cryotherapy, interstitial radioactive seed implantation, external beam irradiation, hyperthermia, gene therapy, cellular therapy, tumor vaccine, or systemically delivered biologic agents or pharmaceuticals.

Another embodiment of the invention is directed to an apparatus for predicting probability of disease recurrence in a patient with prostatic cancer following a radical prostatectomy, wherein the apparatus comprises a correlation of clinical and pathological factors determined for each of a plurality of persons previously diagnosed with prostatic cancer and having been treated by radical prostatectomy with incidence of recurrence of prostatic cancer for each person of said plurality of persons wherein said selected set of factors comprises preoperative PSA level, specimen Gleason sum, prostatic capsular invasion level, surgical margin status, presence of seminal vesicle invasion, and lymph node status; and a means for matching an identical set of factors determined from the patient diagnosed as having prostatic cancer to the correlation to predict the probability of recurrence of prostatic cancer in the patient following radical prostatectomy.

Another embodiment of the invention is directed to a nomogram for the graphic representation of a probability that a patient with prostate cancer will remain free of disease following radical prostatectomy comprising a set of indicia on a solid support, the indicia comprising a preoperative PSA level line, specimen Gleason sum line, a prostatic capsular invasion level line, a surgical margin status line, a presence of seminal vesicle invasion line, a lymph node status line, a points line, a total points line and a predictor line, wherein said preoperative PSA level line, specimen Gleason sum line, prostatic capsular invasion level line, surgical margin status line, presence of seminal vesicle invasion line, and lymph node status line each have values on a scale which can be correlated with values on a scale on the points line, and wherein said total points line has values on a scale which may be correlated with values on a scale on the predictor line, such that the value of each of the points correlating with the patient's preoperative PSA level, specimen Gleason sum, prostatic capsular invasion level, surgical margin status, presence of seminal vesicle invasion, and lymph node status can be added together to yield a total points value, and the total points value can be correlated with the predictor line to predict the probability of recurrence. The solid support may assume any appropriate form such as, for example, a laminated card. Any other suitable representation, picture, depiction or exemplification may be used.

Other embodiments and uses of the invention will be apparent to those skilled in the art from consideration of the specification and practice of the invention disclosed herein. All documents, including U.S. patents and applications disclosed herein and specifically U.S. provisional patent application Ser. No. 60/051,428, are specifically incorporated herein by reference. The specification and example should be considered exemplary only with the true scope and spirit of the invention indicated by the following claims.

What is claimed is:

1. A method for predicting a quantitative probability of recurrence of prostatic cancer following radical prostatectomy in a patient diagnosed as having prostatic cancer comprising the steps of:

correlating a selected set of preoperative factors determined for each of a plurality of persons previously diagnosed with prostatic cancer and having been treated by radical prostatectomy with incidence of recurrence of prostatic cancer for each person of said plurality of persons to generate a functional representation of the correlation, wherein said selected set of preoperative factors comprises pretreatment PSA level, combined Gleason grade and clinical stage, wherein said functional representation of the correlation comprises a pretreatment PSA level scale, a clinical stage scale, a combined Gleason grade scale, a points scale, a total points scale, and a predictor scale, and wherein said pretreatment PSA level scale, said clinical stage scale and said combined Gleason grade scale each have values on said scales which can be correlated with values on the points scale, and wherein said total points scale has values which may be correlated with values on the predictor scale;

determining an identical set of preoperative factors for the patient;

matching the patient's pretreatment PSA level to a corresponding value on the pretreatment PSA level scale, and determining a first point value from the corresponding value on the points scale;

matching the patient's combined Gleason grade to a corresponding value on the combined Gleason grade scale, and determining a second point value from the corresponding value on the points scale;

matching the patient's clinical stage to a corresponding value on the clinical stage scale, and determining a third point value from the corresponding value on the points scale;

adding the first, second and third point values together to get a patient total points value;

matching the patient total points value to a corresponding value on the total points scale; and correlating the corresponding value on the total points scale with a value on the predictor scale to predict the quantitative probability of recurrence of prostatic cancer in the patient following radical prostatectomy.

2. The method of claim 1 wherein the functional representation is a nomogram.

3. The method of claim 2 wherein the nomogram is generated with a Cox proportional hazards regression model.

4. The method of claim 3 wherein the Cox proportional hazards regression model utilizes a Kaplan-Meier method of analysis.

5. The method of claim 2 wherein the nomogram is generated with a neural network model.

6. The method of claim 2 wherein the nomogram is generated with a recursive partitioning model.

7. The method of claim 1 wherein the patient is a pre-surgical candidate.

8. The method of claim 1 wherein the probability of recurrence of prostatic cancer is a probability of remaining free of prostatic cancer five years following radical prostatectomy.

9. The method of claim 1 wherein a recurrence of prostatic cancer is characterized as an increased serum PSA level.

10. The method of claim 9 wherein the increased serum PSA level is greater than or equal to 0.4 ng/mL.

11. The method of claim 1 wherein a recurrence of prostatic cancer is characterized as a positive biopsy, bone scan or the application of further treatment for prostate cancer because of the high probability of subsequent recurrence of the cancer.

12. The method of claim 1 wherein the plurality of persons comprises persons with clinically localized prostate cancer not treated previously by radiotherapy or cryotherapy, and subsequently undergoing radical prostatectomy.

13. The method of claim 1 wherein the selected set of preoperative factors further comprise one or more supplemental factors selected from the group consisting of apoptotic index, maximum cancer length in a core and total length of cancer in the biopsy cores, and said functional representation further comprises one or more supplemental factor scales for each of said one or more supplemental factors, said one or more supplemental factor scales each having values on said scales which can be correlated with the values on the points scale, and wherein said method further comprises the steps of: determining the patient's one or more supplemental factors; matching the patient's one or more supplemental factors to one or more corresponding values on the one or more supplemental factor scales to determine one or more supplemental point values on the points scale; and adding the one or more supplemental point values to the first, second and third point values to determine the patient total points value.

14. A postoperative method for predicting a quantitative probability of recurrence of prostatic cancer in a patient who has previously undergone a radical prostatectomy comprising the steps of:

correlating a selected set of factors determined for each of a plurality of persons previously diagnosed with prostatic cancer with incidence of recurrence of prostatic cancer for each person of said plurality to generate a functional representation of the correlation, wherein said selected set of factors comprises preoperative PSA level, specimen Gleason sum, prostatic capsular invasion level, surgical margin status, presence of seminal vesicle invasion, and lymph node status, wherein said plurality of persons comprises men having undergone radical prostatectomy, wherein said functional representation of the correlation comprises a preoperative PSA level scale, a specimen Gleason sum scale, a prostatic capsular invasion level scale, a surgical margin status scale, a presence of seminal vesicle invasion scale, a lymph node status scale, a points scale, a total points scale, and a predictor scale, and wherein said preoperative PSA level scale, said specimen Gleason sum scale, said prostatic capsular invasion level scale, said surgical margin status scale, said presence of seminal vesicle invasion scale, and said lymph node status scale each have values on said scales which can be correlated with values on the points scale, and wherein said total points scale has values on said scale which may be correlated with values on the predictor scale;

determining an identical set of factors for the patient;

matching the patient's preoperative PSA level to a corresponding value on the preoperative PSA level scale, and determining a first point value from the corresponding value on the points scale;

matching the patient's specimen Gleason sum to a corresponding value on the specimen Gleason sum scale, and determining a second point value from the corresponding value on the points scale;

matching the patient's prostatic capsular invasion level to a corresponding value on the prostatic capsular invasion level scale, and determining a third point value from the corresponding value on the points scale:

matching the patient's surgical margin status to a corresponding value on the surgical margin status scale, and determining a fourth point value from the corresponding value on the points scale;

matching the patient's presence of seminal vesicle invasion to a corresponding value on the presence of seminal vesicle invasion scale, and determining a fifth point value from the corresponding value on the points scale;

matching the patient's lymph node status to a corresponding value on the lymph node status scale, and determining a sixth point value from the corresponding value on the points scale;

adding the first, second, third, fourth, fifth and sixth point values together to get a patient total points value;

matching the patient total points value to a corresponding value on the total points scale, and correlating the corresponding value on the total points scale with a value on the predictor scale to predict the quantitative probability of recurrence of prostatic cancer for the patient.

15. The method of claim 14 wherein the selected set of factors further comprises one or more supplemental factors selected from the group consisting of total tumor volume, zone of location of the cancer, p53, Ki-67, p27, level of extraprostatic extension, DNA ploidy status, type of seminal vesicle invasion, clinical stage and lymphovascular invasion and said functional representation further comprises one or more supplemental factor scales for each of said one or more supplemental factors, said one or more supplemental factor scales each having values on said scales which can be correlated with the values on the points scale, and wherein the method further comprises the steps of: determining the patient's one or more supplemental factors; matching the patient's one or more supplemental factors to one or more corresponding values on the one or more supplemental factor scales to determine one or more supplemental point values on the points scale; and adding the one or more supplemental point values to the first, second, third, fourth, fifth and sixth point values to determine the patient total points value.

16. The method of claim 14 wherein the functional representation is a nomogram.

17. The method of claim 16 wherein the nomogram is generated with a Cox proportional hazards regression model.

18. The method of claim 16 wherein the nomogram is generated with a neural network model.

19. The method of claim 16 wherein the nomogram is generated with a recursive-partitioning model.

20. The method of claim 14 wherein the probability of the recurrence of prostatic cancer is a probability of remaining free of prostatic cancer seven years following radical prostatectomy.

21. The method of claim 14 wherein a recurrence of prostatic cancer is characterized as an increased serum PSA level.

22. The method of claim 14 wherein a recurrence of prostatic cancer is characterized as a positive biopsy, bone scan or the application of further treatment for prostate cancer because of the high probability of subsequent recurrence of the cancer.

23. An apparatus for predicting a quantitative probability of disease recurrence in a patient with prostatic cancer following a radical prostatectomy, wherein the apparatus comprises: a correlation of preoperative factors determined for each of a plurality of persons previously diagnosed with prostatic cancer and having been treated by radical prostatectomy with incidence of recurrence of prostatic cancer for each person of said plurality of persons wherein said selected set of preoperative factors comprises pretreatment PSA level, combined Gleason grade and clinical stage; and a means for comparing an identical set of preoperative factors determined from the patient diagnosed as having prostatic cancer to the correlation to predict the quantitative probability of recurrence of prostatic cancer in the patient following radical prostatectomy.

24. A nomogram for the graphic representation of a quantitative probability that a patient with prostate cancer will remain free of disease following radical prostatectomy comprising a plurality of scales and a solid support, the plurality of scales being disposed on said support and comprising a pretreatment PSA level scale, a clinical stage scale, a combined Gleason grade in the biopsy scale, a points scale, a total points scale and a predictor scale, wherein said pretreatment PSA level scale, clinical stage scale and combined Gleason grade scale each have values on said scales, and wherein said pretreatment PSA level scale, said clinical stage scale and said combined Gleason grade scale are disposed on said solid support with respect to the points scale so that each of said values on said pretreatment PSA level scale, said clinical stage scale and said Gleason grade scale can be correlated with values on the points scale, and wherein said total points scale has values on said total points scale and wherein said total points scale is disposed on said solid support with respect to the predictor scale so that said values on said total points scale may be correlated with values on the predictor scale, such that the values on the points scale correlating with the patient's pretreatment PSA level, combined Gleason grade, and clinical stage can be added together to yield a total points value, and the total points value can be correlated with the predictor scale to predict the quantitative probability of recurrence.

25. A method to predict a preoperative prognosis in a patient comprising: determining a set of preoperative factors comprising the patient's pretreatment PSA level, clinical stage, and combined Gleason grade; matching the preoperative factors to the values on the pretreatment PSA level scale, the clinical stage scale and the combined Gleason grade in the biopsy scale of the nomogram of claim 24; determining a separate point value for each of said preoperative factors: adding the separate point values together to yield a total points value; and correlating the total points value with a value on the predictor scale of said nomogram to determine the preoperative prognosis of the patient.

26. The nomogram of claim 24 wherein the solid support is a laminated card.

27. An apparatus for predicting a quantitative probability of disease recurrence in a patient with prostatic cancer following a radical prostatectomy, wherein the apparatus comprises: a correlation of clinical and pathological factors determined for each of a plurality of persons previously diagnosed with prostatic cancer and having been treated by radical prostatectomy with incidence of recurrence of prostatic cancer for each person of said plurality of persons wherein said selected set of factors comprises preoperative PSA level, specimen Gleason sum, prostatic capsular invasion level, surgical margin status, presence of seminal vesicle invasion, and lymph node status; and a means for comparing an identical set of factors determined from the patient diagnosed as having prostatic cancer to the correlation to predict the quantitative probability of recurrence of prostatic cancer in the patient following radical prostatectomy.

28. A nomogram for the graphic representation of a quantitative probability that a patient with prostate cancer will remain free of disease following radical prostatectomy comprising a plurality of scales and a solid support, the plurality of scales being disposed on said support and comprising a preoperative PSA level scale, a specimen Gleason sum scale, a prostatic capsular invasion level scale, a surgical margin status scale, a presence of seminal vesicle invasion scale, a lymph node status scale, a points scale, a total points scale and a predictor scale, wherein said preoperative PSA level scale, specimen Gleason sum scale, prostatic capsular invasion level scale, surgical margin status scale, presence of seminal vesicle invasion scale, and lymph node status scale each have values on said scales, and wherein said preoperative PSA level scale, said specimen Gleason sum scale, said prostatic capsular invasion level scale, said surgical margin status scale, said presence of seminal vesicle invasion scale, and said lymph node status scale are disposed on said solid support with respect to the points scale so that each of said values on said preoperative PSA level scale, said specimen Gleason sum scale, said prostatic capsular invasion level scale, said surgical margin status scale, said presence of seminal vesicle invasion scale, and said lymph node status scale can be correlated with values on the points scale, and wherein said total points scale has values on said total points scale and wherein said total points scale is disposed on said solid support with respect to the predictor scale so that said values on said total points scale may be correlated with values on the predictor scale, such that the values on the points scale correlating with the patient's preoperative PSA level, specimen Gleason sum, prostatic capsular invasion level, surgical margin status, presence of seminal vesicle invasion, and lymph node status can be added together to yield a total points value, and the total points value can be correlated with the predictor scale to predict the quantitative probability of recurrence.

29. A method to predict a postoperative prognosis in a patient following radical prostatectomy, comprising: determining a set of factors comprising the patient's preoperative PSA level, specimen Gleason sum, prostatic capsular invasion level, surgical margin status, presence of seminal vesicle invasion, and lymph node status; matching the factors to the values on the preoperative PSA level scale, the specimen Gleason sum scale, the prostatic capsular invasion level scale, the surgical margin status scale, the presence of seminal vesicle invasion scale and the lymph node status scale of the nomogram of claim 28; determining a separate point value for each of said factors; adding the separate point values together to yield a total points value; and correlating the total points value with a value on the predictor scale of said nomogram to determine the prognosis of the patient.

30. A method for determining a need for an adjuvant therapy in a patient following radical prostatectomy comprising the steps of: determining a set of factors on the patient, the set of factors comprising the patient's preoperative PSA level, specimen Gleason sum, prostatic capsular invasion level, surgical margin status, presence of seminal vesicle invasion, and lymph node status; matching the set of factors to the values on the preoperative PSA level scale, the specimen Gleason sum scale, the prostatic capsular invasion level scale, the surgical margin status scale, the presence of seminal vesicle invasion scale and the lymph node status scale of the nomogram of claim 26; determining a separate point value for each of said factors; adding the separate point values together to yield a total points value; and correlating the total points value with a value on the predictor scale of said nomogram to determine whether the adjuvant therapy is needed in view of the probability of recurrence.

31. The method of claim 30 wherein the adjuvant therapy comprises radiotherapy.

32. The method of claim 30 wherein the adjuvant therapy is selected from the group of radiotherapy, chemotherapy, hormonal therapy, cryotherapy, interstitial radioactive seed implantation, external beam irradiation, hyperthermia, gene therapy, cellular therapy, tumor vaccines, or systemically delivered biologic agents or pharmaceuticals.

* * * * *